US012746008B2

(12) United States Patent
Lv et al.

(10) Patent No.: US 12,746,008 B2
(45) Date of Patent: Sep. 29, 2026

(54) LIGATION CLIP AND PREPARATION METHOD THEREOF

(71) Applicant: SICHUAN GUONA TECHNOLOGY CO., LTD., Chengdu (CN)

(72) Inventors: Guoyu Lv, Chengdu (CN); Xia Cao, Chengdu (CN); Heng Zheng, Jining (CN)

(73) Assignee: SICHUAN GUONA TECHNOLOGY CO., LTD., Chengdu (CN)

( * ) Notice: Subject to any disclaimer, the term of this patent is extended or adjusted under 35 U.S.C. 154(b) by 0 days.

(21) Appl. No.: 19/081,854

(22) Filed: Mar. 17, 2025

(65) Prior Publication Data

US 2025/0312046 A1 Oct. 9, 2025

Related U.S. Application Data

(63) Continuation of application No. PCT/CN2024/117860, filed on Sep. 10, 2024.

(30) Foreign Application Priority Data

Apr. 7, 2024 (CN) ......................... 202410404240.1

(51) Int. Cl.
*A61B 17/122* (2006.01)

(52) U.S. Cl.
CPC .................................. *A61B 17/122* (2013.01)

(58) Field of Classification Search
CPC ..... A61B 17/08; A61B 17/083; A61B 17/122; A61B 17/1227; A61B 2017/081;
(Continued)

(56) References Cited

U.S. PATENT DOCUMENTS 4,498,476 A * 2/1985 Cerwin ................ A61B 17/122 606/142
4,646,741 A 3/1987 Smith
(Continued)

FOREIGN PATENT DOCUMENTS

CA 2079275 A1 3/1993
CN 10341526 A 11/2013
(Continued)

OTHER PUBLICATIONS

A.P.T. Pezzin et al., "Miscibility and Hydrolytic Degradation of Bioreabsorbable Blends of Poly(p-Dioxanone) and Poly (L-Lactic Acid) Prepared by Fusion" Journal of Applied Polymer Science, vol. 101, No. 3 pp. 18-99-1912 (May 24, 2006).
(Continued)

*Primary Examiner* — Katherine H Schwiker
(74) *Attorney, Agent, or Firm* — SZDC Law PC

(57) ABSTRACT

The present disclosure provides an absorbable biomedical polymer material, a ligating clip, and a method for preparing a ligating clip. In the present disclosure, the absorbable biomedical polymer material is composed of a first polymer and a second polymer, the first polymer consists of 50 wt % to 100 wt % poly-L-lactide and 0 wt % to 50 wt % polyglycolide, and the second polymer is polydioxanone. The absorbable biomedical polymer material has appropriate rigidity and toughness, and may be applied to prepare a medical device such as a ligating clip. The absorbable ligating clip has appropriate rigidity and toughness, especially when it contains 2.5 wt % to 40 wt % of the first polymer, facilitating piercing through a fascia and resisting plastic deformation at a bending point. Finally, the present disclosure further provides some structural forms of the ligating clip and the method for preparing the ligating clip.

20 Claims, 8 Drawing Sheets

(58) Field of Classification Search
CPC .......... A61B 2017/1225; A61B 17/064; A61L 17/00; A61L 17/10; A61L 17/12; A61L 17/005; A61L 17/06; A61L 17/105; A61L 31/148
See application file for complete search history.

(56) References Cited

U.S. PATENT DOCUMENTS

| | | | | |
|---|---|---|---|---|
| 5,470,340 | A | 11/1995 | Bezwada et al. | |
| 6,113,624 | A | 9/2000 | Bezwada et al. | |
| 2002/0177863 | A1* | 11/2002 | Mandel | A61L 17/005 606/158 |
| 2003/0065345 | A1* | 4/2003 | Weadock | A61B 17/0644 606/153 |
| 2008/0114469 | A1* | 5/2008 | O'Brien | A61B 17/08 623/23.76 |
| 2011/0112513 | A1* | 5/2011 | Hester | A61B 17/083 606/228 |
| 2011/0152927 | A1* | 6/2011 | Deng | A61B 17/06166 606/232 |
| 2020/0008810 | A1* | 1/2020 | Patel | A61B 17/1285 |

FOREIGN PATENT DOCUMENTS

| | | | |
|---|---|---|---|
| CN | 105764539 | A | 7/2016 |
| CN | 109982730 | A | 7/2019 |
| CN | 214549510 | U | 11/2021 |
| CN | 116474156 | A | 7/2023 |
| CN | 117982740 | A | 5/2024 |
| GB | 2069848 | A | 9/1981 |

OTHER PUBLICATIONS

Yang Bai et al., "Miscibility, Thermal and Mechanical Properties of Poly(paradioxanone)/Poly(lactic-co-glycolic acid) Blends" J Polym Environ, vol. 23, pp. 367-373 (Jul. 5, 2014).

* cited by examiner

LIGATION CLIP AND PREPARATION METHOD THEREOF

This application is a Continuation application of PCT/CN2024/117860, filed on Sep. 10, 2024, which claims priority to Chinese Patent Application No. 202410404240.1, filed on Apr. 7, 2024, which is incorporated by reference for all purposes as if fully set forth herein.

FIELD

The present disclosure relates to a technical field of biomedical polymer materials, and more particularly, to an absorbable biomedical polymer material, a ligating clip made of the polymer material, and a method for preparing the ligating clip.

BACKGROUND

In the prior art, it is a common practice in the industry to use an absorbable biomedical polymer material, such as polylactic acid, polydioxanone, and polyglycolic acid, to manufacture various medical devices.

For example, a Chinese patent application discloses a bioabsorbable polymer composition, a processing method, and a medical device obtained therefrom. This novel bioabsorbable polymer blend comprises a first component and a second component. The first polymer includes a lactide-rich polymer with a weight ratio about 76 wt % to about 92 wt %. The lactide-rich polymer includes polymerized lactide of 80 mol % to 90 mol % and polymerized glycolide of 10 mol % to 20 mol %. The second polymer is polydioxanone, with a maximum weight percentage of approximately 22 wt %, and its minimum weight percentage depends on a molar amount of polymerized lactide in the lactide-rich polymer. This novel polymer blend provides a medical device with dimensional stability, specifically an injection-molded flat-head staple.

However, this novel polymer blend exhibits high stiffness, but it fails to meet toughness requirements of medical devices such as absorbable ligating devices and tissue engineering scaffolds, making it easily to undergo plastic deformation at the bent part.

Chinese Patent Application: Bioabsorbable Polymer Composition, Processing Method, and Medical Device Obtained Therefrom, Publication Number: CN114316540A, Publication Date: Apr. 12, 2022.

SUMMARY

In view of the deficiencies existing in the prior art mentioned above, the present disclosure aims to provide an absorbable biomedical polymer material with appropriate rigidity and toughness, and a ligating clip made from the polymer material and a method for preparing the ligating clip.

The raw material selected in the present disclosure includes a first polymer and a second polymer. The first polymer is composed of poly-L-lactide with a weight ratio of 50 wt % to 100 wt % and polyglycolide with a weight ratio of 0 wt % to 50 wt %. The second polymer is poly-p-dioxanone.

In the present disclosure, the first polymer and the second polymer are extruded and pelletized by an extruder (preferably a twin-screw extruder) in a nitrogen atmosphere, to prepare the absorbable biomedical polymer material mentioned above. The absorbable biomedical polymer material has appropriate rigidity and toughness, with a tensile strength of 27 to 95.7 MPa, a flexural strength of 23 to 164 MPa, a compressive strength of 95 to 557 MPa, and a Vickers hardness of 2.5 to 19.5 HV.

The absorbable polymer material mentioned above may be mainly applied to preparation of medical devices, and the medical devices also have appropriate rigidity and toughness. Furthermore, the absorbable polymer material mentioned above may be specifically applied to preparation of a ligating clip. Particularly, when the ligating clip includes the first polymer with the weight ratio of 2.5 wt % to 40 wt %, it is easy to pierce a fascia, and it is less likely to undergo plastic deformation at a bent part.

The detailed technical solution of the present disclosure includes the following.

In the present disclosure, the absorbable biomedical polymer material is composed of a first polymer and a second polymer.

With a sum of weight percentages being 100%, the first polymer is composed of poly-L-lactide with a weight ratio of 50 wt % to 100 wt % and polyglycolide with a weight ratio of 0 wt % to 50 wt %; or the first polymer is polymerized from L-lactide with the weight ratio of 50 wt % to 100 wt % and glycolide with the weight ratio of 0 wt % to 50 wt %.

The above alternative solutions only differ in the expressions within the industry, but ultimately convey the same meaning.

The second polymer is poly-p-dioxanone.

Alternatively, the first polymer is composed of the poly-L-lactide with the weight ratio of 70 wt % to 100 wt % and the polyglycolide with the weight ratio of 0 wt % to 30 wt %. The second polymer is poly-p-dioxanone.

Alternatively, the first polymer is composed of the poly-L-lactide with the weight ratio of 50 wt % to 90 wt % and the polyglycolide with the weight ratio of 10 wt % to 50 wt %. The second polymer is poly-p-dioxanone.

Alternatively, the first polymer is composed of the poly-L-lactide with the weight ratio of 70 wt % to 90 wt % and the polyglycolide with the weight ratio of 10 wt % to 25 wt %. The second polymer is poly-p-dioxanone.

Furthermore, the following embodiments with several optional proportions may be available.

With the sum of weight percentages being 100%, the weight ratio of the first polymer is 0 wt % to 80 wt %, and the weight ratio of the second polymer is 20 wt % to 100 wt %.

With the sum of weight percentages being 100%, the weight ratio of the first polymer is 2.5 wt % to 80 wt %, and the weight ratio of the second polymer is 20 wt % to 97.5 wt %.

With the sum of weight percentages being 100%, the weight ratio of the first polymer is 2.5 wt % to 70 wt %, and the weight ratio of the second polymer is 30 wt % to 97.5 wt %.

With the sum of weight percentages being 100%, the weight ratio of the first polymer is 2.5 wt % to 60 wt %, and the weight ratio of the second polymer is 40 wt % to 97.5 wt %.

With the sum of weight percentages being 100%, the weight ratio of the first polymer is 2.5 wt % to 50 wt %, and the weight ratio of the second polymer is 50 wt % to 97.5 wt %.

With the sum of weight percentages being 100%, the weight ratio of the first polymer is 2.5 wt % to 40 wt %, and the weight ratio of the second polymer is 60 wt % to 97.5 wt %.

With the sum of weight percentages being 100%, the weight ratio of the first polymer is 2.5 wt % to 35 wt %, and the weight ratio of the second polymer is 65 wt % to 97.5 wt %.

Based on the same inventive concept, the present disclosure further provides a method for preparing the absorbable biomedical polymer material, to obtain the absorbable biomedical polymer material mentioned above. The first polymer and the second polymer are extruded and pelletized by a twin-screw extruder in a nitrogen atmosphere at a temperature of 140° C.-160° C., preferably in a nitrogen atmosphere at 150° C.

The medical devices made from the polymer material mainly include sutures, suspension threads, self-suturing stent nails, flat-head nails, clips, suture threads, patches, substrates, meshes, tissue engineering scaffolds, ligating clips, drug delivery devices.

Specifically, when preparing the ligating clip, the pellet obtained after co-extrusion of the absorbable biomedical polymer material may be injection-molded by an injection molding machine. Four temperature zones of the injection molding machine may be configured to 30° C. to 60° C., 130° C. to 150° C., 140° C. to 160° C., and 150° C. to 170° C. respectively. In a specific implementation, the four temperature zones may be selected as 40° C., 140° C., 150° C., and 160° C.

Based on the same inventive concept, the present disclosure further provides a ligating clip, which is obtained by injection-molding the pellet obtained after co-extrusion of the absorbable biomedical polymer material by using an injection molding machine.

The ligating clip includes a ligating clip body. The ligating clip body includes a clip and a locking device for keeping the clip closed.

The clip has a first clip arm and a second clip arm connected in a V-shape. The first clip arm and the second clip arm are in a curved arc structure with a same direction, or the first clip arm and the second clip arm are in a straight structure.

Furthermore, an inward arc-shaped protrusion is provided in the middle of an inner side where the first clip arm and the second clip arm face each other, and the middle of an outer side where the first clip arm and the second clip arm are opposite to each other is a flat surface.

Furthermore, an inward arc-shaped protrusion is provided in the middle of an inner side where the first clip arm and the second clip arm face each other, and an inward arc-shaped depression is provided in the middle of the outer side where the first clamping arm and the second clamping arm are opposite to each other.

Furthermore, an anti-slip teeth or an anti-slip groove is provided on an inner surface of the first clip arm and the second clip arm where they face each other.

Furthermore, a hollow groove is provided at the connection part of the first clip arm and the second clip arm.

Furthermore, the clip is further provided with a clamping device.

The clamping device includes a first clamping column arranged on left and right sides of the distal end of the first clip arm along a width direction of the clip, and a second clamping column arranged on left and right sides of the distal end of the second clip arm along the width direction of the clip.

Furthermore, the clip is further provided with a positioning device.

The positioning device includes a first positioning groove provided on an inner side of the distal end of the first clip arm and a first positioning protrusion provided on an inner side of the second clip arm and adapted to the first positioning groove, and/or the positioning device comprises a second positioning protrusion provided on an outer side of the distal end of the second clip arm and a second positioning groove provided on an outer side of the first clip arm and adapted to the second positioning protrusion Furthermore, the clip is integrally formed by injection molding.

Furthermore, the locking device includes a hook portion arranged at a distal end of the first clip arm and a fitting portion arranged at a distal end of the second clip arm and adapted to the hook portion. The hook portion is provided with an acute-angle cutting structure or a linear sharp-edge cutting structure.

Furthermore, the locking device further includes two limit blocks. The two limit blocks are oppositely arranged at the distal end of the second clip arm. The hook portion is engaged with the two limit blocks and is limited between the two limit blocks.

Furthermore, the locking device is further provided with a penetrating device configured to cut a tissue when the clip begins to close. The penetrating device comprises a pointed cutting head provided at an outer end of the hook portion. When the clip begins to close, the pointed cutting head cooperates with an inclined surface on the fitting portion to cut the tissue.

The present disclosure further provides a ligating clip with a further structure. The ligating clip includes a ligating clip body. The ligating clip body includes an inner clip and an outer clip with a U shape. When the inner clip is inserted into the U-shaped inner area of the outer clip, clamping is completed. The outer clip and the inner clip are obtained by respectively injection-molding the pellet obtained after co-extrusion of the absorbable biomedical polymer material by using an injection molding machine. The content of the first polymer in the outer clip is greater than that in the inner clip.

Furthermore, an outer wall of the inner clip has a groove along a length direction of the inner clip, and an inner wall of a U-shaped area of the outer clip has a rib matching with the groove. When the rib is inserted into the groove and slides along the groove, the inner clip is forcibly deformed within the outer clip to complete clamping.

Based on the same inventive concept, the present disclosure further provides a ligating clip with antibacterial efficacy. The ligating clip includes a ligating clip body which has the same structure as the aforementioned ligating clip, and an antibacterial agent uniformly dispersed in the ligating clip body. During preparation, the antibacterial agent is uniformly dispersed in the raw material first. After processing or injection molding, the antibacterial agent is uniformly distributed throughout the ligating clip, and may be released slowly during the degradation process of the ligating clip body. The weight of the antibacterial agent accounts for 0.1 wt % to 10 wt % of the total weight of the ligating clip body.

In a further implementation, the present disclosure further provides a ligating clip with antibacterial efficacy. The ligating clip includes a ligating clip body which has the same structure as the aforementioned ligating clip, and an antibacterial layer attached to the surface of the ligating clip body. The antibacterial layer includes an antibacterial agent, and the weight of the antibacterial agent accounts for 0.1 wt % to 3 wt % of the total weight of the ligating clip body.

Furthermore, the antibacterial agent is one or more of a halogenated hydroxy ether, an acyloxy diphenyl ether, a vanillin, an ethyl vanillin compound, an acyl aniline, an imidazole, a thiazole, an isothiazolone derivative, a quaternary ammonium salt, a biguanide, and a phenol.

Furthermore, the antibacterial agent is a nanoparticle containing any one or a combination of metal ions of silver, cerium, and zinc. Alternatively, the antibacterial agent is one or more of a tetracycline hydrochloride, a neomycin sulfate, a chloramphenicol, a streptomycin sulfate, a penicillin potassium, an oxytetracycline hydrochloride, a gentamicin sulfate, a cephalothin sodium, a furanone, a rifamycin, a benzalkonium chloride, an oxacillin sodium, a dihydrostreptomycin sulfate, a carbenicillin disodium, and a nitrofurantoin sodium.

Furthermore, the antibacterial agent is 2,4,4'-trichloro-2'-hydroxydiphenyl ether.

Furthermore, the composition of the antibacterial layer further includes an adhesive and a lubricant.

The beneficial effects of the present disclosure include the following.

Firstly, the absorbable biomedical polymer material provided in the present disclosure is composed of the first polymer and the second polymer. With the sum of weight percentages being 100%, the first polymer is composed of poly-L-lactide with the weight ratio of 50 wt % to 100 wt % and polyglycolide with the weight ratio of 0 wt % to 50 wt %, and the second polymer is poly-p-dioxanone. The absorbable biomedical polymer material has certain rigidity and toughness, with a tensile strength of 27 to 95.7 MPa, a flexural strength of 23 to 164 MPa, a compressive strength of 95 to 557 MPa, and a Vickers hardness of 2.5 to 19.5 HV.

Secondly, the ligating clip provided in the present disclosure may effectively address the defects of poor toughness in similar materials and poor hardness in existing absorbable ligating clip materials. It may pierce through the fascia during use and improve its mechanical property.

REFERENCE SIGNS

Figure 1:
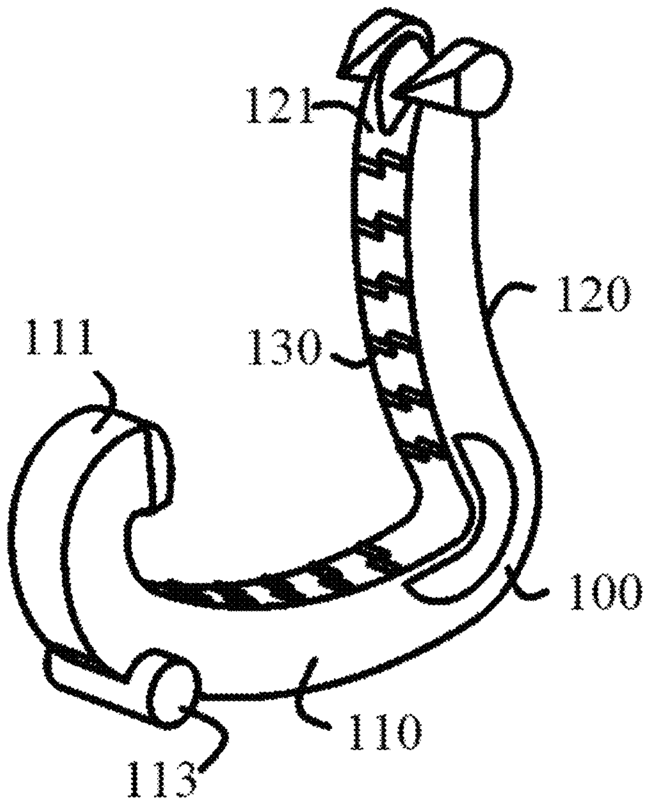
FIG. 1 is a structural schematic diagram of a ligating clip in a first form according to Embodiment 2 of the present disclosure.

100: clip; 110: first clip arm; 111: hook portion; 112: pointed cutting head; 113: first clamping column; 114: first positioning groove; 115: reinforcing rib

120: second clip arm; 121: fitting portion; 122: second clamping column; 123: first positioning protrusion;

130: anti-slip teeth; 140: limit block;

200: inner clip; 201: groove

300: outer clip; 301: rib

DETAILED DESCRIPTION

Merely some exemplary embodiments are briefly described below. As those skilled in the art can recognize, the embodiments described may be modified in various different ways without departing from the spirit or scope of the embodiments of the present disclosure. Therefore, the drawings and the description are considered to be illustrative in nature rather than restrictive.

The terms "first" and "second" are only used for descriptive purposes and should not be construed as indicating or implying relative importance or implicitly indicating the number of the indicated technical features. Thus, a feature defined as "first" or "second" may explicitly or implicitly include one or more of such features.

In the embodiments of the present disclosure, unless otherwise clearly defined and limited, terms such as "install" and "connect" should be understood in a broad sense. For example, it may be a direct connection or an indirect connection through an intermediate medium, and it may be the internal communication of two components or the interaction relationship between two components. For those of ordinary skill in the art, they may understand the specific meanings of the above terms in the embodiments of the present disclosure according to specific situations.

Various different implementation manners or examples are provided below for implementing different structures of the embodiments of the present disclosure. In order to simplify the disclosure of the embodiments of the present disclosure, the components and settings of specific examples are described below. Certainly, they are only examples and are not intended to limit the embodiments of the present disclosure. In addition, the embodiments of the present disclosure may repeat reference numbers in different examples, and this repetition is for the purpose of simplification and clarity, and it does not indicate the relationship between the various implementation manners being discussed.

Embodiment 1

In this embodiment, an absorbable biomedical polymer material is provided, which is composed of a first polymer and a second polymer.

With the sum of the weight percentages being 100%, the first polymer is composed of poly-L-lactide (PLA) with a weight ratio of 50 wt % to 100 wt % and polyglycolide (PGA) with a weight ratio of 0 wt % to 50 wt %, and has an intrinsic viscosity of 1.9-3.5 dL/g, hereinafter referred to as PLLGA for short. The second polymer is poly-p-dioxanone, with an intrinsic viscosity of 1.5-2.5 dL/g (preferably 1.9), hereinafter referred to as PPDO for short.

Furthermore, with the sum of the weight percentages being 100%, the first polymer is composed of poly-L-lactide (PLA) with a weight ratio of 70 wt % to 100 wt % and polyglycolide (PGA) with a weight ratio of 0 wt % to 30 wt %, and has an intrinsic viscosity of 1.9-3.5 dL/g. The second polymer is poly-p-dioxanone, with an intrinsic viscosity of 1.5-2.5 dL/g (preferably 1.9).

Furthermore, with the sum of the weight percentages being 100%, the first polymer is composed of poly-L-lactide (PLA) with a weight ratio of 50 wt % to 90 wt % and polyglycolide (PGA) with a weight ratio of 10 wt % to 50 wt %, and has an intrinsic viscosity of 1.9-3.5 dL/g. The second polymer is poly-p-dioxanone, with an intrinsic viscosity of 1.5-2.5 dL/g (preferably 1.9).

Furthermore, with the sum of the weight percentages being 100%, the first polymer is composed of poly-L-lactide (PLA) with a weight ratio of 75 wt % to 90 wt % and polyglycolide (PGA) with a weight ratio of 10 wt % to 25 wt %, and has an intrinsic viscosity of 1.9-3.5 dL/g. The second polymer is poly-p-dioxanone, with an intrinsic viscosity of 1.5-2.5 dL/g (preferably 1.9).

Preferably, with the sum of the weight percentages being 100%, the weight ratio of the first polymer is 0 wt % to 80 wt %, and the weight ratio of the second polymer is 20 wt % to 100 wt %.

More preferably, the weight ratio of the first polymer is 2.5 wt % to 80 wt %, and the weight ratio of the second polymer is 20 wt % to 97.5 wt %.

More preferably, the weight ratio of the first polymer is 2.5 wt % to 60 wt %, and the weight ratio of the second polymer is 40 wt % to 97.5 wt %.

More preferably, the weight ratio of the first polymer is 2.5 wt % to 50 wt %, and the weight ratio of the second polymer is 50 wt % to 97.5 wt %.

Even more preferably, the weight ratio of the first polymer is 2.5 wt % to 40 wt %, and the weight ratio of the second polymer is 60 wt % to 97.5 wt %.

Even more preferably, the weight ratio of the first polymer is 2.5 wt % to 35 wt %, and the weight ratio of the second polymer is 65 wt % to 97.5 wt %.

In this embodiment, a method for preparing an absorbable biomedical polymer material is further provided to obtain the absorbable biomedical polymer material. It is obtained by extruding and pelletizing the first polymer and the second polymer by using a twin-screw extruder in a nitrogen atmosphere at a temperature of 140° C.-160° C. Through testing and comparison, a better effect is achieved when it is prepared in a nitrogen atmosphere at 150° C.

The absorbable biomedical polymer material prepared by the aforementioned method may be used for medical devices including sutures, suspension threads, self-suturing stent nails, flat-head nails, clips, suture threads, patches, substrates, meshes, tissue engineering scaffolds, ligating clips, drug delivery devices, etc.

To prepare the aforementioned medical devices, the pellet obtained after co-extrusion of the absorbable biomedical polymer material may be injection-molded by an injection molding machine. During injection molding, the temperature ranges of the four temperature zones in the injection molding machine may be set to 30° C. to 60° C., 130° C. to 150° C., 140° C. to 160° C., and 150° C. to 170° C. respectively. In a specific implementation scenario, if the four temperature zones are specifically set to 40° C., 140° C., 150° C., and 160° C., the prepared medical devices have better rigidity and toughness that meet expectations.

The absorbable biomedical polymer material will be described below with further examples.

According to the ratio, the two polymer pellets of PLLGA and/or PPDO are physically mixed first. Then, the mixture obtained is re-pelletized by a twin-screw extruder under nitrogen protection at 150° C. Subsequently, the re-pelletized polymer blend material is added to the barrel of the injection molding machine. The four temperature zones of the injection molding machine are set to 40° C., 140° C., 150° C., and 160° C. respectively. Standard test specimens are prepared via injection molding, and their mechanical properties are tested after annealing at 60-80° C. for 8 hours.

During the test, three standard test specimens with the same ratio may be taken for testing, and the average value of the test results may be used as the detection result. The relevant detection results are shown in Tables 1-8.

During tensile testing, the loading rate is 3 mm/min. During bending testing, the loading rate is 1 mm/min. During compression testing, the loading rate is 1 mm/min, and the compression degree is 90%.

In Tables 1-4, for the standard test specimens (sample numbers 1-12), the composition of PLLGA is 85 wt % of PLA and 15 wt % of PGA. The weight percentages of PLLGA are 0%, 2.5%, 5%, 10%, 20%, 35%, 40%, 50%, 60%, 70%, 80%, and 100% respectively. The difference lies in the different weight percentages of PLLGA and PPDO.

In Tables 5-8, for the standard test specimens (sample numbers 13-18), the composition is 40 wt % of PLLGA and 60 wt % of PPDO. The difference lies in the different weight percentages of PLA and PGA in PLLGA.

TABLE 1

Tensile data of standard specimens with sample numbers 1-12

| Sample No | Tensile Strength/ MPa | Elastic Modulus/ MPa | Elongation at Break/% | Mean Tensile Strength/ MPa | Mean Elastic Modulus/ MPa | Mean Elongation at Break/% | PLLGA Content |
|---|---|---|---|---|---|---|---|
| 1-1 | 32 | 285.29 | 381.42 | 32.80 | 292.60 | 387.12 | 0% |
| 1-2 | 33 | 297.89 | 408.52 | | | | |
| 1-3 | 33.4 | 294.61 | 371.42 | | | | |
| 2-1 | 34 | 324.63 | 330.67 | 35.04 | 331.65 | 345.44 | 2.50% |
| 2-2 | 34.91 | 330.38 | 358.33 | | | | |

TABLE 1-continued

Tensile data of standard specimens with sample numbers 1-12

| Sample No | Tensile Strength/ MPa | Elastic Modulus/ MPa | Elongation at Break/% | Mean Tensile Strength/ MPa | Mean Elastic Modulus/ MPa | Mean Elongation at Break/% | PLLGA Content |
|---|---|---|---|---|---|---|---|
| 2-3 | 36.2 | 339.94 | 347.33 | | | | |
| 3-1 | 36.92 | 343.41 | 326.75 | 38.00 | 347.34 | 294.94 | 5% |
| 3-2 | 38.37 | 347.19 | 286.83 | | | | |
| 3-3 | 38.72 | 351.42 | 271.25 | | | | |
| 4-1 | 39.88 | 409.01 | 234.50 | 41.02 | 408.06 | 242.89 | 10% |
| 4-2 | 41.57 | 406.89 | 250.58 | | | | |
| 4-3 | 41.61 | 408.28 | 243.58 | | | | |
| 5-1 | 41.91 | 422.12 | 226.00 | 42.17 | 420.53 | 230 | 20% |
| 5-2 | 42.01 | 411.48 | 224.17 | | | | |
| 5-3 | 42.58 | 427.76 | 239.83 | | | | |
| 6-1 | 43.02 | 428.05 | 213.01 | 43.53 | 428.8 | 215.66 | 35% |
| 6-2 | 43.56 | 429.70 | 214.33 | | | | |
| 6-3 | 44.01 | 428.66 | 219.63 | | | | |
| 7-1 | 44.84 | 430.05 | 206.49 | 46.43 | 449.53 | 209.72 | 40% |
| 7-2 | 46.21 | 441.53 | 217.44 | | | | |
| 7-3 | 48.25 | 477.02 | 205.24 | | | | |
| 8-1 | 51.36 | 733.12 | 175.09 | 51.45 | 759.19 | 165.99 | 50% |
| 8-2 | 50.96 | 762.33 | 163.22 | | | | |
| 8-3 | 52.03 | 782.11 | 159.66 | | | | |
| 9-1 | 53.19 | 982.63 | 211.42 | 63.87 | 1015.44 | 133.14 | 60% |
| 9-2 | 68.02 | 1052.87 | 93.17 | | | | |
| 9-3 | 70.41 | 1010.82 | 94.83 | | | | |
| 10-1 | 75.36 | 1190.11 | 57.23 | 74.93 | 1183.51 | 51.41 | 70% |
| 10-2 | 76.12 | 1153.69 | 55.76 | | | | |
| 10-3 | 73.31 | 1206.75 | 41.25 | | | | |
| 11-1 | 77.23 | 1312.48 | 29.00 | 83.50 | 1302.28 | 24.97 | 80% |
| 11-2 | 85.42 | 1280.09 | 21.42 | | | | |
| 11-3 | 87.86 | 1314.26 | 24.50 | | | | |
| 12-1 | 94.81 | 1427.81 | 12.00 | 95.66 | 1450.43 | 13.5 | 100% |
| 12-2 | 95.41 | 1465.82 | 16.83 | | | | |
| 12-3 | 96.75 | 1457.65 | 11.67 | | | | |

TABLE 2

Bending data of standard specimens for sample numbers 1~12

| Sample No | Bending Strength/MPa | Bending Modulus/MPa | Mean Bending Strength/MPa | Mean Bending Modulus/MPa | PLLGA Content |
|---|---|---|---|---|---|
| 1-1 | 69.98 | 283.04 | 71.15 | 266.65 | 0% |
| 1-2 | 71.13 | 247.89 | | | |
| 1-3 | 72.34 | 269.01 | | | |
| 2-1 | 72.56 | 285.40 | 74.39 | 289.29 | 2.50% |
| 2-2 | 75.17 | 252.33 | | | |
| 2-3 | 75.44 | 330.15 | | | |
| 3-1 | 76.46 | 524.10 | 76.93 | 399.18 | 5% |
| 3-2 | 77.05 | 423.03 | | | |
| 3-3 | 77.28 | 250.41 | | | |
| 4-1 | 77.82 | 461.30 | 78.89 | 452.37 | 10% |
| 4-2 | 79.29 | 281.34 | | | |
| 4-3 | 79.57 | 614.46 | | | |
| 5-1 | 79.92 | 731.26 | 80.46 | 590.00 | 20% |
| 5-2 | 80.48 | 477.03 | | | |
| 5-3 | 80.97 | 561.73 | | | |
| 6-1 | 81.36 | 1009.12 | 82.03 | 1024.36 | 35% |
| 6-2 | 82.03 | 960.36 | | | |
| 6-3 | 82.69 | 1103.61 | | | |
| 7-1 | 81.05 | 1349.99 | 84.31 | 1355.16 | 40% |
| 7-2 | 83.79 | 1365.95 | | | |
| 7-3 | 88.1 | 1349.55 | | | |
| 8-1 | 106.36 | 1722.53 | 109.29 | 1764.24 | 50% |
| 8-2 | 110.25 | 1766.91 | | | |
| 8-3 | 111.27 | 1803.26 | | | |
| 9-1 | 133.52 | 2431.47 | 137.1 | 2321.87 | 60% |
| 9-2 | 136.48 | 2396.35 | | | |
| 9-3 | 141.3 | 2137.78 | | | |

TABLE 2-continued

| Bending data of standard specimens for sample numbers 1~12 | | | | | |
|---|---|---|---|---|---|
| Sample No | Bending Strength/MPa | Bending Modulus/MPa | Mean Bending Strength/MPa | Mean Bending Modulus/MPa | PLLGA Content |
| 10-1 | 143.66 | 2596.33 | 145.78 | 2666.35 | 70% |
| 10-2 | 145.69 | 2697.36 | | | |
| 10-3 | 147.99 | 2705.36 | | | |
| 11-1 | 150.62 | 3107.21 | 153 | 3132.19 | 80% |
| 11-2 | 152.77 | 3177.22 | | | |
| 11-3 | 155.62 | 3112.13 | | | |
| 12-1 | 157.57 | 3317.38 | 163.89 | 3480.41 | 100% |
| 12-2 | 162.34 | 3548.28 | | | |
| 12-3 | 171.75 | 3575.58 | | | |

TABLE 3

| Compression data of standard specimens with sample numbers 1-12 | | | | | |
|---|---|---|---|---|---|
| Sample No | Compressive Strength/MPa | Elastic Modulus/MPa | Mean Compressive Strength/MPa | Mean Elastic Modulus/MPa | PLLGA Content |
| 1-1 | 94.27 | 136.72 | 95.86 | 138.32 | 0% |
| 1-2 | 94.68 | 134.82 | | | |
| 1-3 | 98.63 | 143.41 | | | |
| 2-1 | 112.35 | 161.37 | 116.04 | 158.90 | 2.50% |
| 2-2 | 115.7 | 155.58 | | | |
| 2-3 | 120.06 | 159.76 | | | |
| 3-1 | 122.02 | 198.34 | 128.45 | 208.43 | 5% |
| 3-2 | 123.41 | 205.46 | | | |
| 3-3 | 139.91 | 221.5 | | | |
| 4-1 | 141.54 | 229.94 | 144.48 | 227.84 | 10% |
| 4-2 | 142.86 | 208.58 | | | |
| 4-3 | 149.05 | 245.01 | | | |
| 5-1 | 179.85 | 262.03 | 172.36 | 246.47 | 20% |
| 5-2 | 162.43 | 222.03 | | | |
| 5-3 | 174.8 | 255.35 | | | |
| 6-1 | 321.22 | 711.02 | 319.03 | 708.91 | 35% |
| 6-2 | 326.74 | 725.36 | | | |
| 6-3 | 309.12 | 690.36 | | | |
| 7-1 | 369.56 | 815.18 | 377.78 | 829.11 | 40% |
| 7-2 | 389.5 | 887.89 | | | |
| 7-3 | 374.27 | 784.26 | | | |
| 8-1 | 399.56 | 893.63 | 402.68 | 906.9 | 50% |
| 8-2 | 402.36 | 912.01 | | | |
| 8-3 | 406.11 | 915.06 | | | |
| 9-1 | 417.85 | 932.32 | 423.91 | 951.06 | 60% |
| 9-2 | 421.3 | 978.1 | | | |
| 9-3 | 432.58 | 942.77 | | | |
| 10-1 | 429.22 | 936.14 | 434.72 | 938.92 | 70% |
| 10-2 | 435.69 | 939.37 | | | |
| 10-3 | 439.25 | 941.25 | | | |
| 11-1 | 436.45 | 908.3 | 453.32 | 937.75 | 80% |
| 11-2 | 454.34 | 949.18 | | | |
| 11-3 | 469.16 | 955.76 | | | |
| 12-1 | 492.48 | 986.84 | 501.39 | 1023.95 | 100% |
| 12-2 | 498.27 | 1032.14 | | | |
| 12-3 | 513.43 | 1052.86 | | | |

TABLE 4

| Vickers hardness data of standard specimens with sample numbers 1-12 | | | | | |
|---|---|---|---|---|---|
| Sample No | Maximum Hardness Value | Minimum Hardness Value | Standard Deviation | Average Value | PLLGA Content |
| 1 | 6.3 | 6.3 | 0 | 6.3 | 0% |
| 2 | 6.3 | 6.3 | 0 | 6.3 | 2.50% |
| 3 | 6.4 | 6.4 | 0 | 6.4 | 5% |
| 4 | 6.5 | 6.4 | 0.1 | 6.5 | 10% |
| 5 | 6.7 | 6.6 | 0.1 | 6.7 | 20% |
| 6 | 7.3 | 7.2 | 0.1 | 7.3 | 35% |
| 7 | 7.6 | 7.1 | 0.2 | 7.4 | 40% |
| 8 | 9.3 | 9.2 | 0.1 | 9.2 | 50% |
| 9 | 12.9 | 12.3 | 0.4 | 12.7 | 60% |
| 10 | 13.3 | 13.2 | 0.1 | 13.2 | 70% |
| 11 | 13.9 | 13.2 | 0.4 | 13.5 | 80% |
| 12 | 19.4 | 18.9 | 0.3 | 19.1 | 100% |

TABLE 5

| Tensile data of standard specimens with sample numbers 13-18 | | | | | | | |
|---|---|---|---|---|---|---|---|
| Sample No | Tensile Strength/ MPa | Elastic Modulus/ MPa | Elongation at Break mm/% | Mean Tensile Strength/ MPa | Mean Elastic Modulus/ MPa | Mean Elongation at Break (mm/%) | PLA Content |
| 13-1 | 29.15 | 142.88 | 988.59 | 27.65 | 144.10 | 877.74 | 50% |
| 13-2 | 28.33 | 146.97 | 830.66 | | | | |
| 13-3 | 25.47 | 142.46 | 813.96 | | | | |
| 14-1 | 31.44 | 391.61 | 404.61 | 31.83 | 392.5 | 409.53 | 75% |
| 14-2 | 28.62 | 384.02 | 344.19 | | | | |
| 14-3 | 35.44 | 401.87 | 479.80 | | | | |
| 15-1 | 40.25 | 403.13 | 226.63 | 40.08 | 418.54 | 227.26 | 82% |
| 15-2 | 38.92 | 452.65 | 198.70 | | | | |
| 15-3 | 41.08 | 399.85 | 256.44 | | | | |
| 16-1 | 44.84 | 430.05 | 206.49 | 46.43 | 449.53 | 209.72 | 85% |
| 16-2 | 46.21 | 441.53 | 217.44 | | | | |
| 16-3 | 48.25 | 477.02 | 205.24 | | | | |
| 17-1 | 47.36 | 531.22 | 175.03 | 46.97 | 556.51 | 167.09 | 90% |
| 17-2 | 46.56 | 545.36 | 169.23 | | | | |
| 17-3 | 46.99 | 592.95 | 157.02 | | | | |
| 18-1 | 46.87 | 635.32 | 189.61 | 47.84 | 628.32 | 150.65 | 100% |
| 18-2 | 48.15 | 625.6 | 143.81 | | | | |
| 18-3 | 48.51 | 624.04 | 118.53 | | | | |

TABLE 6

| Bending data of standard specimens with sample numbers 13-18 | | | | | |
|---|---|---|---|---|---|
| Sample No | Bending Strength/MPa | Bending Modulus/MPa | Mean Bending Strength/MPa | Mean Bending Modulus/MPa | PLA Content |
| 13-1 | 25.31 | 239.48 | 23.48 | 215.31 | 50% |
| 13-2 | 21.79 | 179.22 | | | |
| 13-3 | 23.34 | 227.22 | | | |
| 14-1 | 71.30 | 657.79 | 77.83 | 656.91 | 75% |
| 14-2 | 92.35 | 690.88 | | | |
| 14-3 | 69.86 | 622.07 | | | |
| 15-1 | 82.40 | 1254.76 | 81.97 | 1303.93 | 82% |
| 15-2 | 82.06 | 1270.05 | | | |
| 15-3 | 81.44 | 1387.00 | | | |
| 16-1 | 81.05 | 1349.99 | 84.31 | 1355.16 | 85% |
| 16-2 | 83.79 | 1365.95 | | | |
| 16-3 | 88.1 | 1349.55 | | | |
| 17-1 | 98.28 | 1459.11 | 98.33 | 1459.78 | 90% |
| 17-2 | 101.36 | 1496.36 | | | |
| 17-3 | 95.36 | 1423.87 | | | |
| 18-1 | 126.01 | 1625.69 | 119.17 | 1676.61 | 100% |
| 18-2 | 88.42 | 1719.43 | | | |
| 18-3 | 143.08 | 1684.71 | | | |

TABLE 7

Compression data of standard specimens with sample numbers 13-18

| Sample No | Compressive Strength/MPa | Elastic Modulus/MPa | Mean Compressive Strength/MPa | Mean Elastic Modulus/MPa | PLA Content |
|---|---|---|---|---|---|
| 13-1 | 204.84 | 676.69 | 226.75 | 697.61 | 50% |
| 13-2 | 221.51 | 695.73 | | | |
| 13-3 | 253.9 | 720.42 | | | |
| 14-1 | 299.63 | 748.11 | 277.37 | 718.80 | 75% |
| 14-2 | 263.53 | 622.69 | | | |
| 14-3 | 268.94 | 785.60 | | | |
| 15-1 | 354.14 | 820.78 | 333.91 | 804.75 | 82% |
| 15-2 | 310.12 | 751.90 | | | |
| 15-3 | 337.48 | 841.58 | | | |
| 16-1 | 369.56 | 815.18 | 377.78 | 829.11 | 85% |
| 16-2 | 389.5 | 887.89 | | | |
| 16-3 | 374.27 | 784.26 | | | |
| 17-1 | 423.68 | 936.17 | 441.19 | 957.45 | 90% |
| 17-2 | 436.39 | 956.39 | | | |
| 17-3 | 463.51 | 979.79 | | | |
| 18-1 | 542.47 | 1240.19 | 556.84 | 1258.35 | 100% |
| 18-2 | 547.12 | 1262.57 | | | |
| 18-3 | 580.92 | 1272.30 | | | |

TABLE 8

Vickers hardness data of samples with sample numbers 13-18

| Sample No | Hardness Value (HV) | Mean Hardness Value | PLA Content |
|---|---|---|---|
| 13-1 | 2.8 | 2.57 | 50% |
| 13-2 | 2.4 | | |
| 13-3 | 2.5 | | |
| 14-1 | 7.5 | 7.37 | 75% |
| 14-2 | 7.4 | | |
| 14-3 | 7.2 | | |
| 15-1 | 8.0 | 7.83 | 82% |
| 15-2 | 7.6 | | |
| 15-3 | 7.9 | | |
| 16-1 | 7.6 | 7.80 | 85% |
| 16-2 | 7.9 | | |
| 16-3 | 7.9 | | |
| 17-1 | 8.9 | 8.9 | 90% |
| 17-2 | 8.7 | | |
| 17-3 | 9.1 | | |
| 18-1 | 9.8 | 9.83 | 100% |
| 18-2 | 10.1 | | |
| 18-3 | 9.6 | | |

It may be known from the data in the table that by adjusting the weight ratios of PLLGA and PPDO, and the weight ratios of PLA and PGA in PLLGA, an absorbable biomedical polymer material with appropriate rigidity and toughness may be obtained, which meets the usage requirements of medical devices.

Embodiment 2

In this embodiment, a ligating clip is provided. The ligating clip is obtained by injection-molding the pellet obtained after co-extrusion of the absorbable biomedical polymer material.

The absorbable biomedical polymer material is composed of a first polymer and a second polymer.

With the sum of the weight percentages being 100%, the first polymer is composed of poly-L-lactide (PLA) with a weight ratio of 50 wt % to 100 wt % and polyglycolide (PGA) with a weight ratio of 0 wt % to 50 wt %, and has an intrinsic viscosity of 1.9-3.5 dL/g, hereinafter referred to as PLLGA for short.

The second polymer is poly-p-dioxanone, with an intrinsic viscosity of 1.5-2.5 dL/g (preferably 1.9), hereinafter referred to as PPDO for short.

Preferably, in an embodiment, with the sum of the weight percentages being 100%, the weight ratio of the first polymer is 2.5 wt % to 80 wt %, and the weight ratio of the second polymer is 20 wt % to 97.5 wt %.

More preferably, in other embodiments, with the sum of the weight percentages being 100%, the weight ratio of the first polymer is 2.5 wt % to 60 wt %, and the weight ratio of the second polymer is 40 wt % to 97.5 wt %.

More preferably, in other embodiments, with the sum of the weight percentages being 100%, the weight ratio of the first polymer is 2.5 wt % to 50 wt %, and the weight ratio of the second polymer is 50 wt % to 97.5 wt %.

More preferably, in other embodiments, with the sum of the weight percentages being 100%, the weight ratio of the first polymer is 2.5 wt % to 40 wt %, and the weight ratio of the second polymer is 60 wt % to 97.5 wt %.

More preferably, in other embodiments, with the sum of the weight percentages being 100%, the weight ratio of the first polymer is 2.5 wt % to 35 wt %, and the weight ratio of the second polymer is 65 wt % to 97.5 wt %.

The ligating clip includes a ligating clip body, which further includes a clip 100 and a locking device for keeping the clip 100 closed.

The clip 100 has a first clip arm 110 and a second clip arm 120 connected in a V shape. The first clip arm 110 and the second clip arm 120 are integrally injection-molded or connected at the proximal end by an elastic hinge. An anti-slip teeth 130 or anti-slip groove is provided on an inner surface of the first clip arm 110 and the second clip arm 120 where they face each other.

The locking device includes a hook portion 111 arranged at the distal end of the first clip arm 110 and a fitting portion 121 arranged at the distal end of the second clip arm 120 and adapted to the hook portion 111. The locking device is further provided with a penetrating device configured to cut the tissue when the clip 100 begins to close. The penetrating device comprises a pointed cutting head 112 provided at an outer end of the hook portion 111. When the clip 100 begins to close, the pointed cutting head 112 cooperates with the inclined surface on the fitting portion 121 to cut the tissue.

The clip 100 further has a clamping device. The clamping device includes a first clamping column 113 arranged on left and right sides of the distal end of the first clip arm 110 along a width direction of the clip 100, and/or a second clamping column 122 arranged on left and right sides of the distal end of the second clip arm 120 along the width direction of the clip 100.

Figure 2:
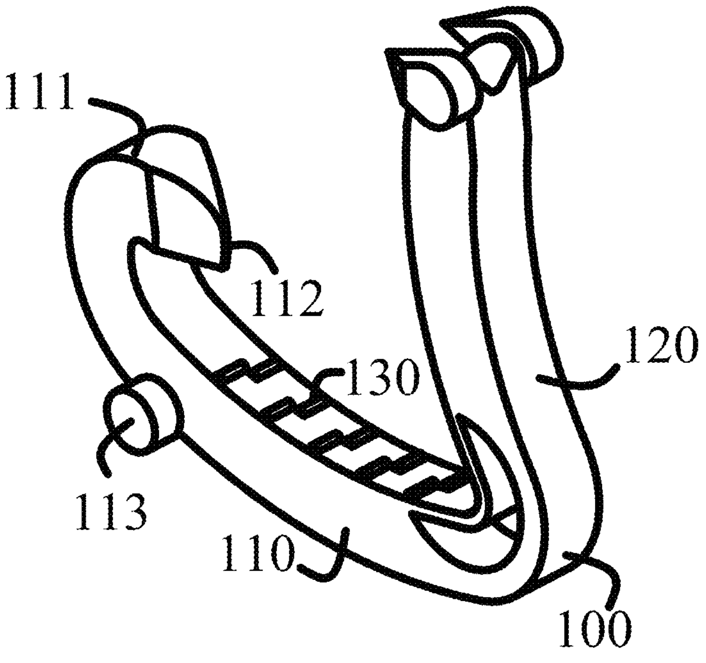
FIG. 2 is a schematic diagram of a ligating clip in the first form from other angles according to Embodiment 2 of the present disclosure.
Figure 3:
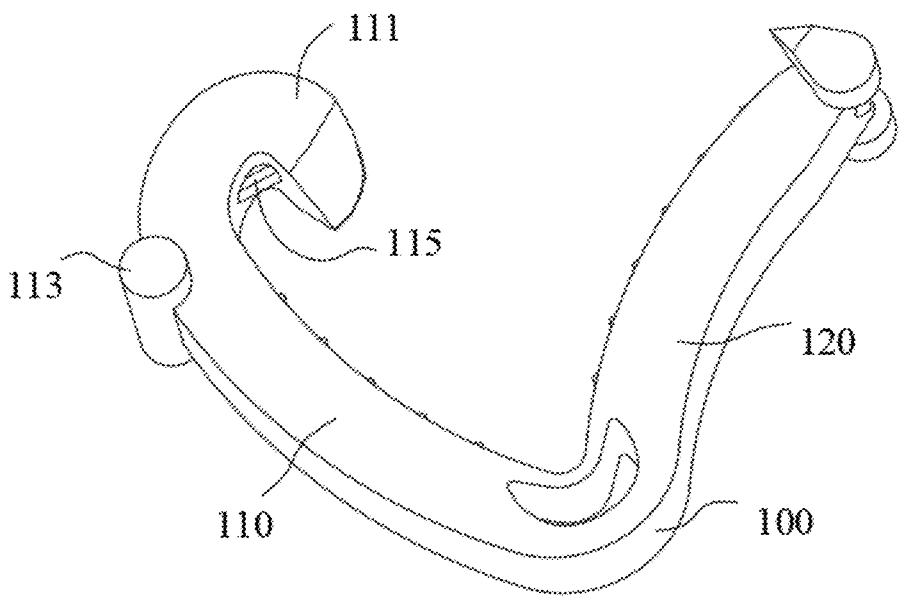
FIG. 3 is a schematic diagram of an improved structure (with a reinforcing rib) of a ligating clip in the first form according to Embodiment 2 of the present disclosure.

FIGS. 1-3 show a ligating clip with the first form in this embodiment. The first clip arm 110 and the second clip arm 120 are in a curved arc structure with a same direction. A hollow groove is provided at the connection part the first clip arm 110 and the second clip arm 120. Compared with the ligating clips shown in FIGS. 1 and 2, the ligating clip shown in FIG. 3 has a reinforcing rib 115 provided on the inner side of the hook portion 111 (that is, the ligating clips shown in FIGS. 1 and 2 have no reinforcing rib 115 on the inner side of the hook portion 111), which is mainly used to strengthen the strength of the hook portion 111 and prevent side slipping after the first clip arm 110 and the second clip arm 120 are clamped closed.

Figure 4:
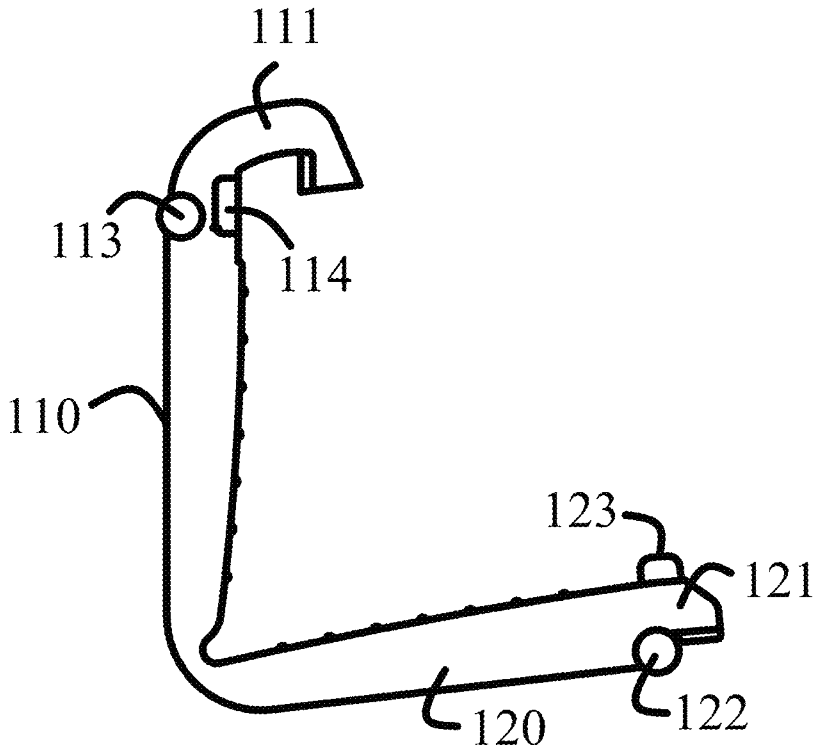
FIG. 4 is a side view of a ligating clip in a second form according to Embodiment 2 of the present disclosure.
Figure 5:
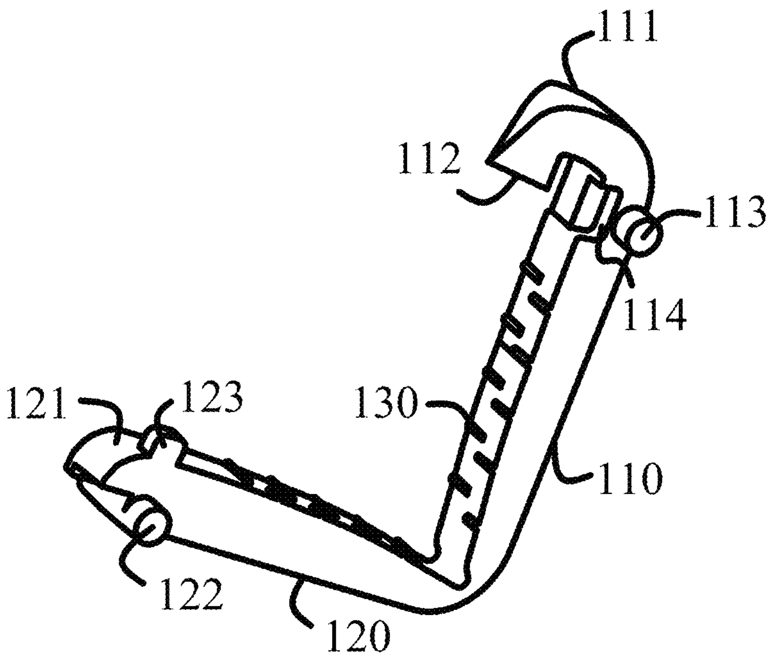
FIG. 5 is a structural schematic diagram of the ligating clip in the second form according to Embodiment 2 of the present disclosure.

FIGS. 4-5 show the ligating clip with the second form in this embodiment. Both the first clip arm 110 and the second clip arm 120 have a straight structure. A positioning device is provided on the clip 100. The positioning device includes a first positioning groove 114 provided on the inner side of the distal end of the first clip arm 110 and a first positioning protrusion 123 provided on the inner side of the second clip arm 120 and adapted to the first positioning groove 114.

Figure 6:
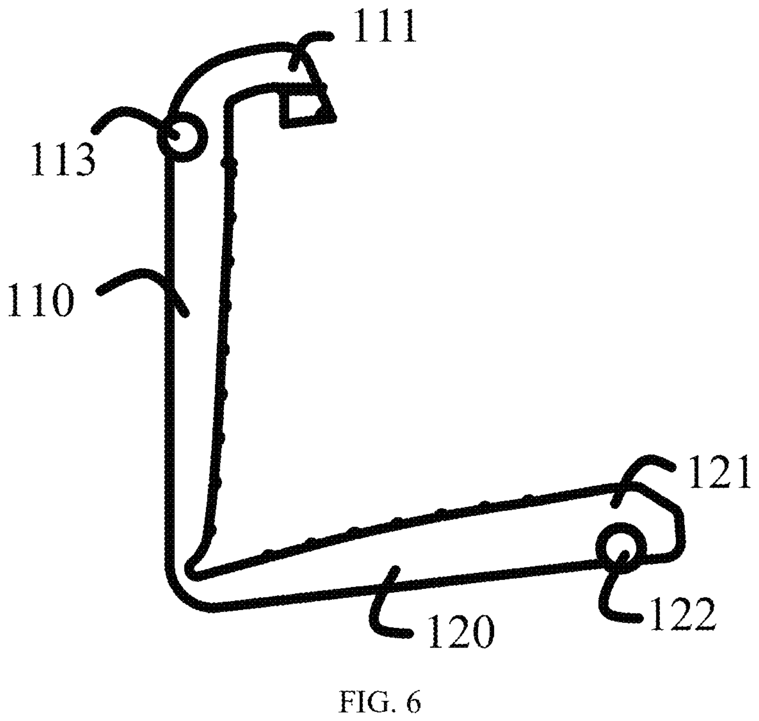
FIG. 6 is a side view of a ligating clip in a third form according to Embodiment 2 of the present disclosure.
Figure 7:
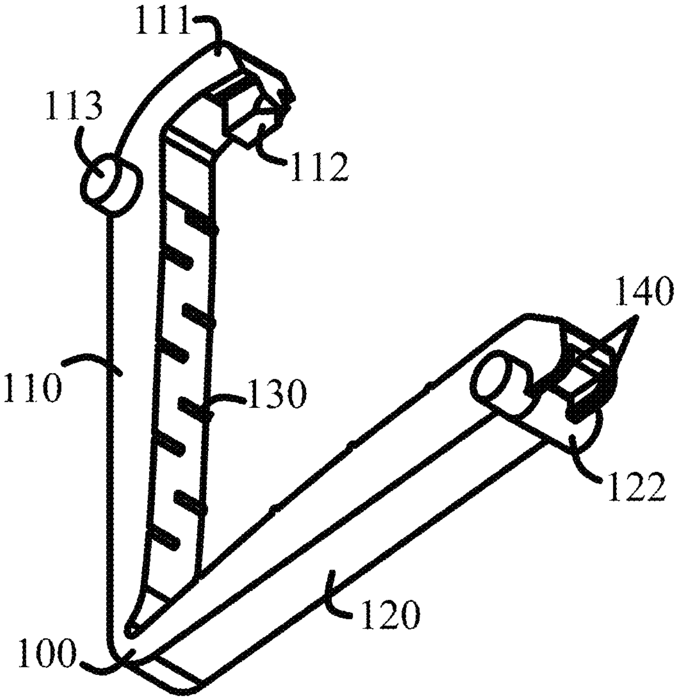
FIG. 7 is a structural schematic diagram of a ligating clip in a third form according to Embodiment 2 of the present disclosure.

FIGS. 6-7 show the ligating clip with the third form in this embodiment. Both the first clip arm 110 and the second clip arm 120 have a straight structure. An inward arc-shaped protrusion is provided in the middle of the inner side where the first clip arm 110 and the second clip arm 120 face each other, and the middle of the outer side where the first clip arm 110 and the second clip arm 120 are opposite to each other is a flat surface.

The ligating clip of this structural form is provided with an acute-angle cutting structure at the hook portion 111. In addition, furthermore, the locking device is further provided with two limiting blocks 140. The two limiting blocks 140 are oppositely arranged at the distal end face of the second clip arm 120. The hook portion 111 is engaged with the two limit blocks 140 and is limited between the two limit blocks 140.

Figure 8:
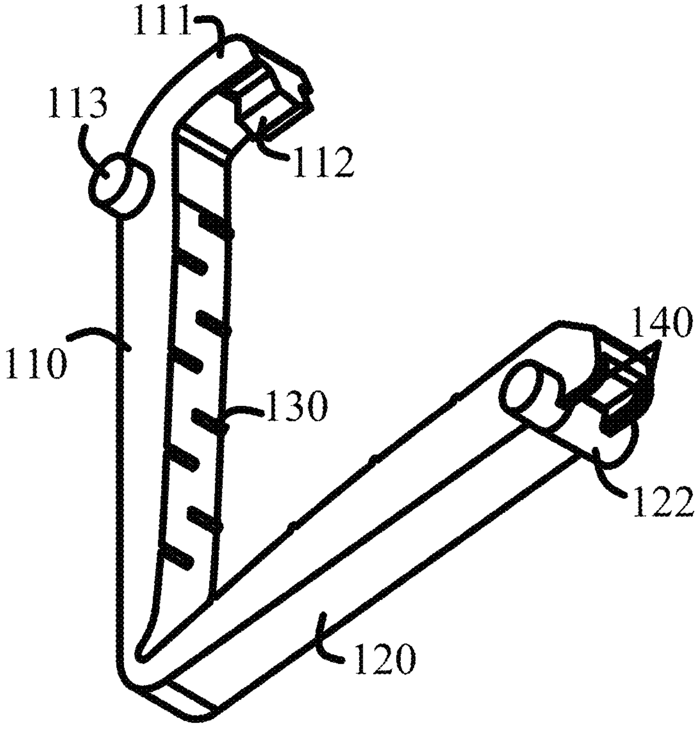
FIG. 8 is a structural schematic diagram of a ligating clip in a fourth form according to Embodiment 2 of the present disclosure.

FIG. 8 shows the ligating clip with the fourth form in this embodiment. Both the first clip arm 110 and the second clip arm 120 have a straight structure. Moreover, the middle parts of the opposite inner sides of the first clip arm 110 and the second clip arm 120 are both inward arc-shaped protrusions. The middle parts of the opposite outer sides of the first clip arm 110 and the second clip arm 120 are both flat.

Compared with the ligating clip with the structural form shown in FIG. 7, the difference lies in that the cutting structure at the hook portion 111 is a linear sharp-edge cutting structure. The other structures are basically the same. In other words, similarly, the locking device is also provided with two limiting blocks 140, and the two limiting blocks 140 are oppositely arranged at the outer surface of the distal end of the second clip arm 120. The hook portion 111 is engaged with the two limiting blocks 140 and is limited between the two limiting blocks 140.

Figure 9:
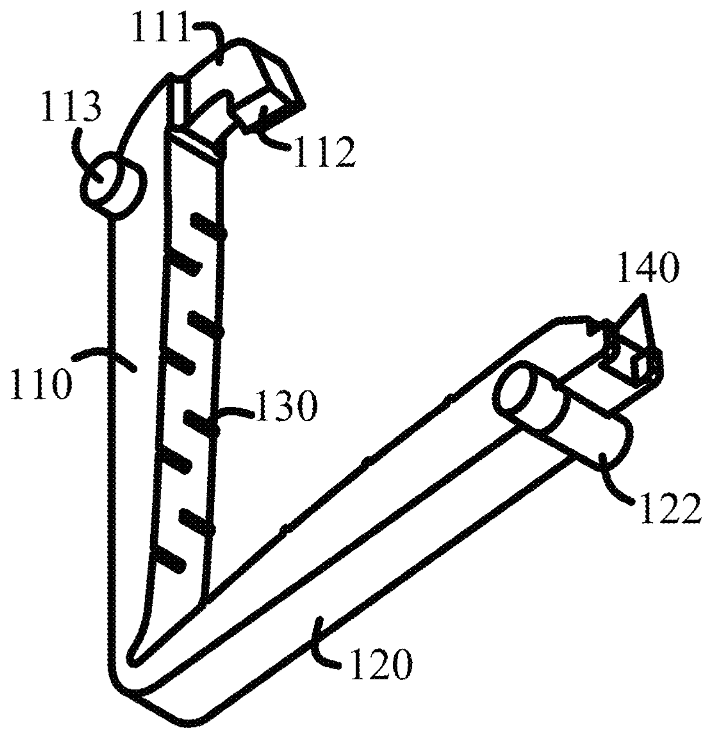
FIG. 9 is a structural schematic diagram of a ligating clip in a fifth form according to Embodiment 2 of the present disclosure.

FIG. 9 shows the ligating clip with the fifth form in this embodiment. Both the first clip arm 110 and the second clip arm 120 have a straight structure. Moreover, the middle parts of the opposite inner sides of the first clip arm 110 and the second clip arm 120 are both inward arc-shaped protrusions. The middle parts of the opposite outer sides of the first clip arm 110 and the second clip arm 120 are both flat. The hook portion 111 is provided with a linear sharp-edge cutting structure. The locking device is further provided with two limiting blocks 140, and the two limiting blocks 140 are oppositely arranged on the distal end face of the second clip arm 120. The hook portion 111 is engaged with the two limiting blocks 140 and is limited between the two limiting blocks 140.

Figure 10:
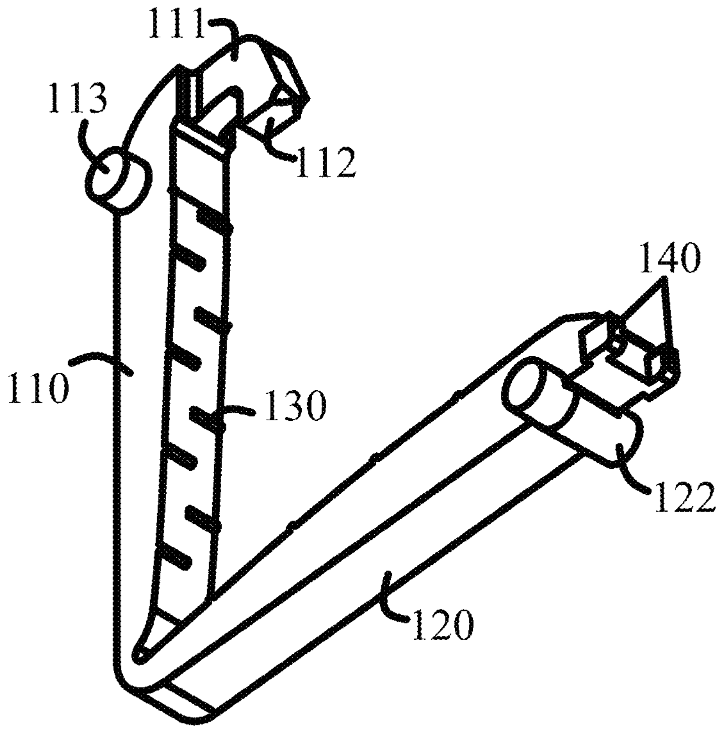
FIG. 10 is a structural schematic diagram of a ligating clip in a sixth form according to Embodiment 2 of the present disclosure.

FIG. 10 shows the ligating clip with the sixth form in this embodiment. Both the first clip arm 110 and the second clip arm 120 have a straight structure. Moreover, the middle parts of the opposite inner sides of the first clip arm 110 and the second clip arm 120 are both inward arc-shaped protrusions. The middle parts of the opposite outer sides of the first clip arm 110 and the second clip arm 120 are both flat.

Compared with the ligating clip with the structural form shown in FIG. 9, the difference lies in that the cutting structure at the hook portion 111 is an acute-angle cutting structure. The hook portion 111 is provided with an acute-angle cutting structure, which is slightly different from the formation manner of the hook portion 111 of the previous ligating clip, and the other parts are basically the same. That is, the locking device is also provided with two limiting blocks 140, and the two limiting blocks 140 are oppositely arranged at the distal end face of the second clip arm 120. The hook portion 111 is engaged with the two limiting blocks 140 and is limited between the two limiting blocks 140.

Figure 14:
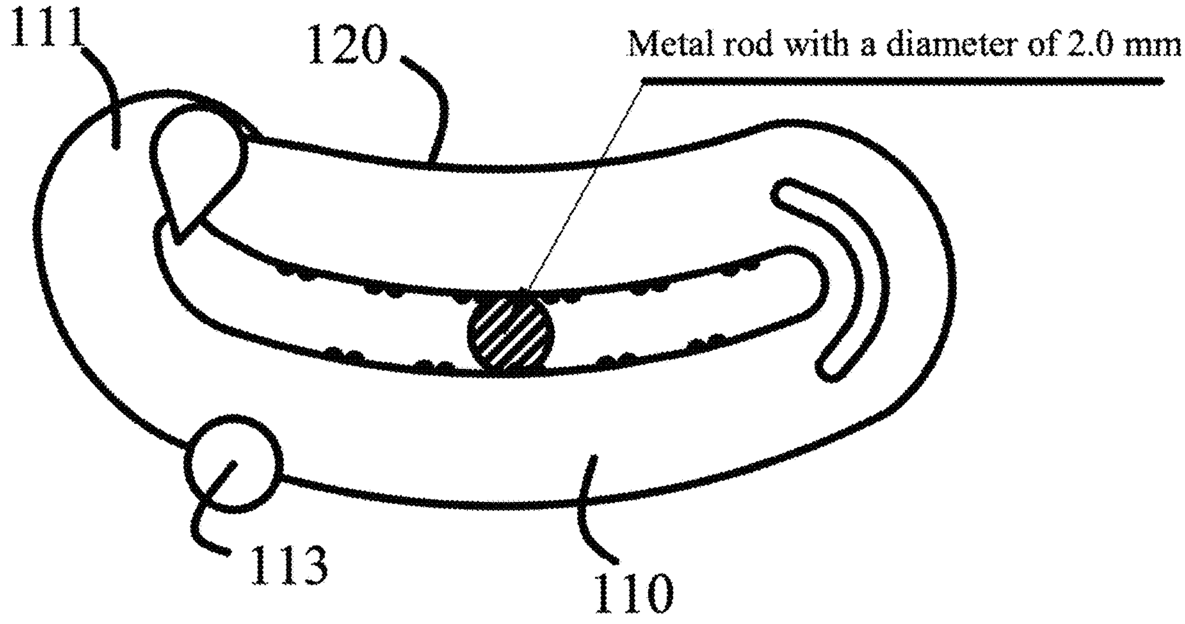
FIG. 14 a schematic diagram illustrating a test for clamping a cylindrical metal rod when testing a clamping range and brittle fracture performance of the ligating clip according to Embodiment 2 of the present disclosure.
Figure 15:
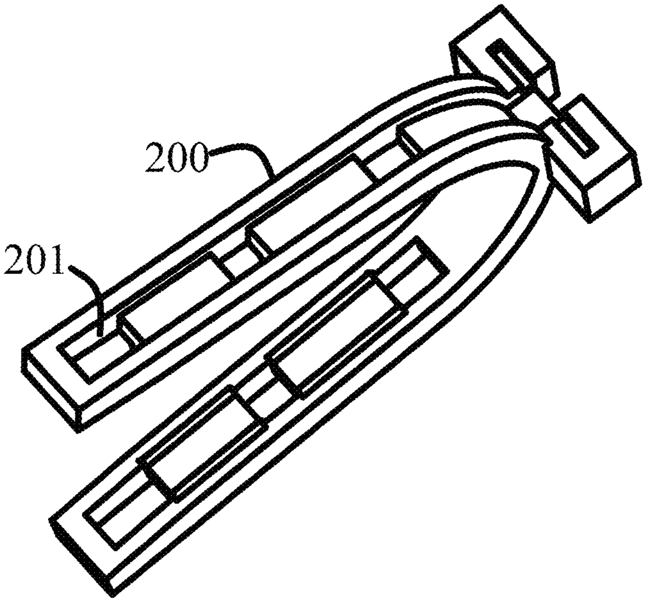
FIG. 15 is a structural schematic diagram of an outer clip of a ligating clip in a seventh form according to Embodiment 2 of the present disclosure.
Figure 16:
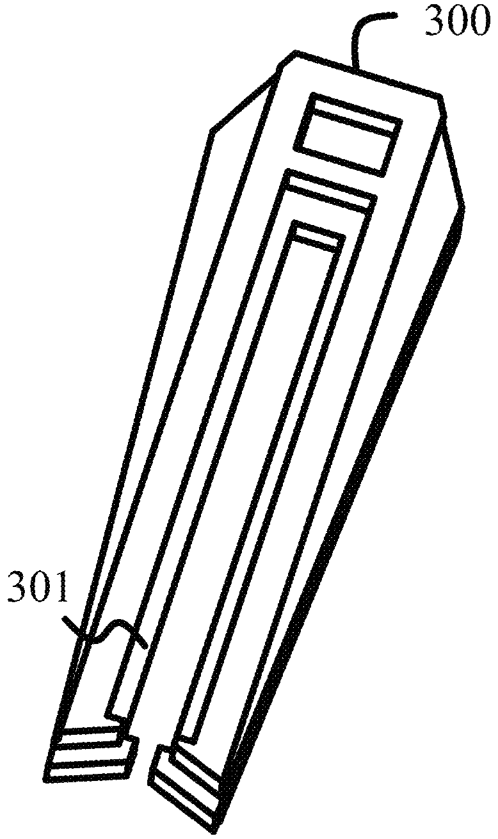
FIG. 16 is a structural schematic diagram of an inner clip of the ligating clip in the seventh form according to Embodiment 2 of the present disclosure.

FIGS. 14-15 show the ligating clip with the seventh structural form shown in this embodiment, which includes an inner clip 200 and an outer clip 300 with a U shape. The outer wall of the inner clip 200 has a groove 201 along its length direction. The inner wall of the U-shaped area of the outer clip 300 has a rib 301 that cooperates with the groove 201. When the rib 301 is inserted into the groove 201 and slides along the groove 201, the inner clip 200 is forcibly deformed to be within the outer clip 300, and the clamping is gradually completed.

The outer clip 300 and the inner clip 200 are obtained by respectively injection-molding the pellet obtained after co-extrusion of the absorbable biomedical polymer material by using an injection molding machine.

The absorbable biomedical polymer material is composed of a first polymer and a second polymer. With the sum of the weight percentages being 100%, the first polymer is composed of poly-L-lactide (PLA) with a weight ratio of 70 wt % to 100 wt % and polyglycolide (PGA) with a weight ratio of 0 wt % to 30 wt %, and has an intrinsic viscosity of 1.9-3.5 dL/g, hereinafter referred to as PLLGA for short. The second polymer is poly-p-dioxanone, with an intrinsic viscosity of 1.9 dL/g, hereinafter referred to as PPDO for short. Preferably, with the sum of the weight percentages being 100%, the weight ratio of the first polymer is 2.5 wt % to 80 wt %, and the weight ratio of the second polymer is 20 wt % to 97.5 wt %. More preferably, with the sum of the weight percentages being 100%, the weight ratio of the first polymer is 2.5 wt % to 50 wt %, and the weight ratio of the second polymer is 50 wt % to 97.5 wt %. The content of the first polymer in the outer clip 300 is greater than that in the inner clip 200. Even more preferably, with the sum of the weight percentages being 100%, the weight ratio of the first polymer in the outer clip 300 is 40 wt % to 70 wt %, and the weight ratio of the second polymer is 30 wt % to 60 wt %. With the sum of the weight percentages being 100%, the weight ratio of the first polymer in the inner clip 200 is 2.5 wt % to 10 wt %, and the weight ratio of the second polymer is 90 wt % to 97.5 wt %.

In this embodiment, taking the ligating clip in the first form as an example, multiple samples are injection-molded and tested for springback performance, anti-slip-off ability, clamping range and brittle fracture performance. The composition of PLLGA in the samples is all 85 wt % of PLA and 15 wt % of PGA, and the weight ratios of PLLGA (the ratio of PLLGA to PPDO) are 0%, 10%, 15%, 20%, 30%, 40%, 50%, 60%, 80%, and 100% respectively.

When using the ligating clip in laparoscopic surgery, it needs to first enter the abdominal cavity through the trocar in a semi-closed state, and will not fall off the clip applier when it is reopened, and it should still maintain good tension, such that it will not fall off or tilt from the clip applier when it touches other soft tissues during the surgery. Therefore, the springback performance of the ligating clip when it returns to the free state after being semi-closed is important.

Figure 11:
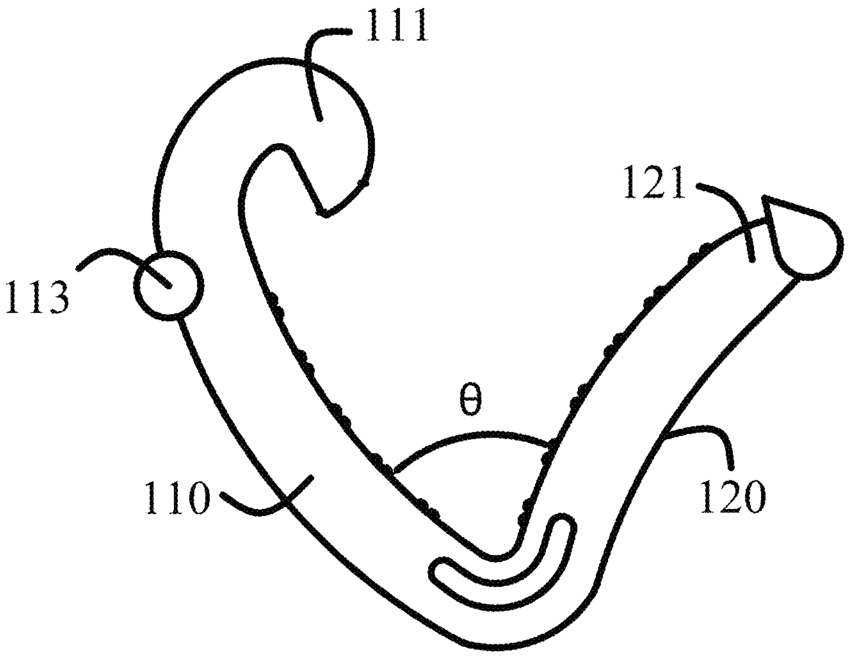
FIG. 11 is a structural schematic diagram of a ligating clip in a free state according to Embodiment 2 of the present disclosure.
Figure 12:
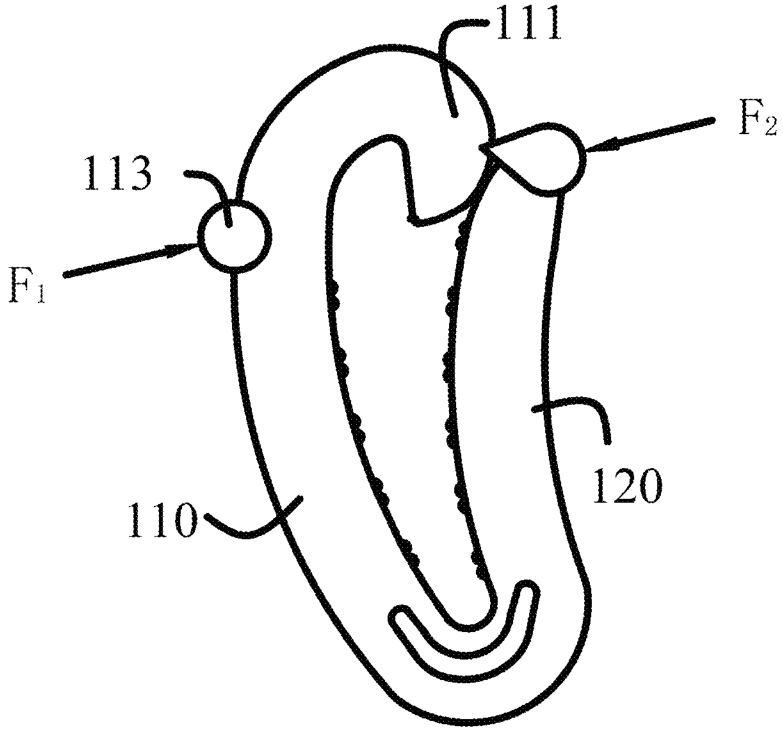
FIG. 12 is a structural schematic diagram of a ligating clip in a semi-closed state according to Embodiment 2 of the present disclosure.

The test method for springback performance includes the following. As shown in FIGS. 11-12, FIG. 11 (the ligating clip shown in FIG. 11 has no reinforcing rib 115) shows the ligating clip in the free state. When it is deformed and closed under the action of the force F to become the semi-closed state shown in FIG. 12, and then the force F is removed, the ligating clip will return to the free state due to its own elasticity. However, due to the simultaneous plastic deformation during the semi-closed process, the ligating clip may not fully return to the initial free state shown in FIG. 10, but the angle θ between the two arms will become smaller. The more times it is semi-closed, the smaller the angle θ will be. When it reaches the limit $\theta_f$, the ligating clip will fall off from the tool that holds it and lose its surgical value.

The springback performance of materials with different formulation ratios varies greatly. Table 9 shows the test results of the springback performance when PLLGA accounts for different proportions in the composite material.

TABLE 9

Table of effective springback times of semi-closure unit: times

| | PLLGA ratio (wt %) | | | | | | | | | |
|---|---|---|---|---|---|---|---|---|---|---|
| | 0 | 10 | 15 | 20 | 30 | 40 | 50 | 60 | 80 | 100 |
| Sample 1 | 32 | 28 | 21 | 18 | 8 | 5 | 2 | 2 | 1 | 0 |
| Sample 2 | 38 | 30 | 23 | 14 | 6 | 4 | 2 | 1 | 0 | 0 |
| Sample 3 | 22 | 29 | 20 | 17 | 11 | 6 | 3 | 1 | 1 | 0 |
| Sample 4 | 27 | 32 | 19 | 16 | 7 | 5 | 2 | 2 | 1 | 0 |
| Sample 5 | 33 | 27 | 17 | 16 | 9 | 3 | 1 | 1 | 0 | 0 |
| mean number of times | 30 | 29 | 20 | 16 | 8 | 4.6 | 2 | 1.5 | 0.5 | 0 |

It is found from the above table that when the proportion of PLLGA is between 0 wt % and 40 wt %, the number of effective semi-closures is relatively large, and it has good use value. For the composite materials with the proportion of PLLGA between 40 wt % and 80 wt %, although they have a certain springback performance, it is not very ideal, but they can still be used reluctantly. The materials with a proportion of PLLGA above 80 wt % have poor springback performance and no use value.

When the ligating clip clamps the tubular or strip-shaped biological tissue during the operation, it should not slip off during or after the operation. Therefore, it is necessary to increase the positive pressure of the ligating clip on the ligated tissue after closure and the lateral anti-slip ability.

Figure 13:
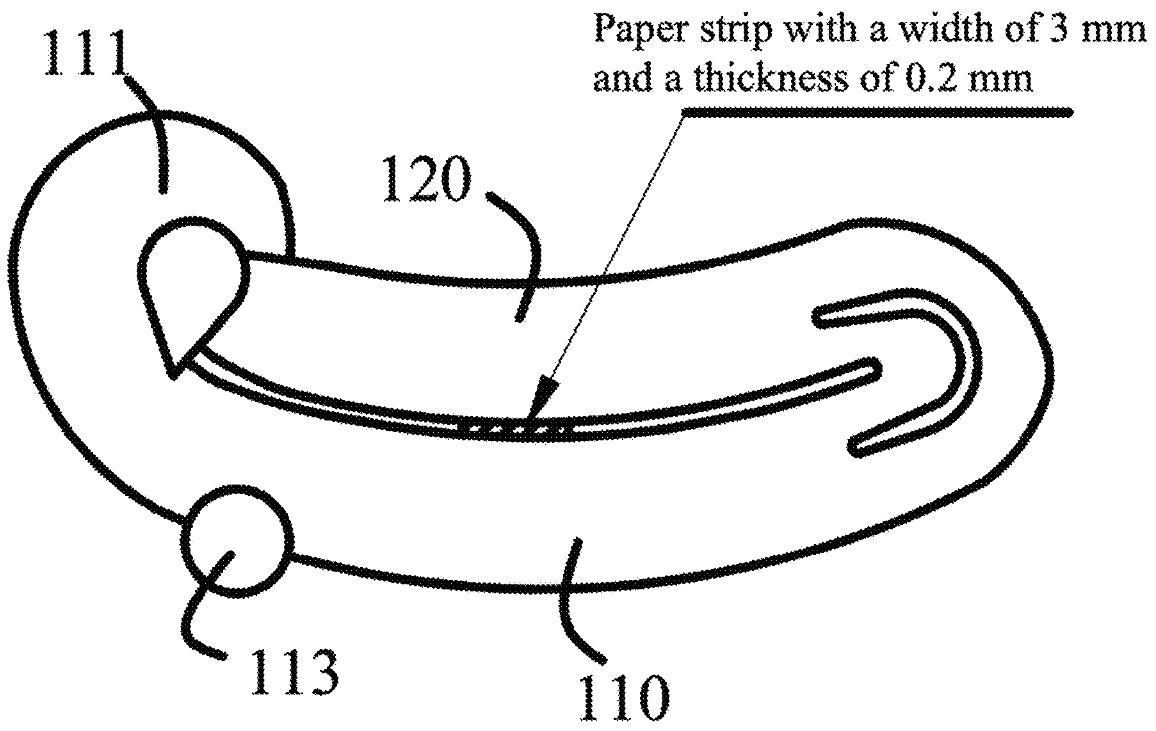
FIG. 13 is a schematic diagram illustrating a test for clamping a strip-shaped object when testing an anti-slip performance of the ligating clip according to Embodiment 2 of the present disclosure.

The anti-slip-off ability test is performed. As shown in FIG. 13, a strip with a thickness of 0.2 mm and a width of 3 mm is used as the clamped object. After the strip is clamped by the ligating clip (the clamping position is the same each time), the ligating clip is fixed, and one end of the strip is pulled with a tensiometer (the other end is in a free state) to make it slide on the closed contact surface of the ligating clip. In this case, the pulling force is the maximum anti-slip pulling force. The greater the pulling force value is, the better the anti-slip performance is, and the tighter the clamping is. Table 10 shows the test conclusions of the anti-slip-off ability test when PLLGA accounts for different proportions in the composite material.

TABLE 10

Pulling force value data

| | PLLGA ratio (wt %) | | | | | | | | | |
|---|---|---|---|---|---|---|---|---|---|---|
| | 0 | 10 | 15 | 20 | 30 | 40 | 50 | 60 | 80 | 100 |
| Sample 1 | 3.2 | 3.2 | 3.5 | 4.2 | 5.9 | 6.9 | 8.4 | 8.8 | 11.4 | 14.8 |
| Sample 2 | 2.8 | 2.9 | 4.5 | 4.3 | 4.7 | 5.7 | 8.6 | 10.0 | 11.8 | 12.7 |
| Sample 3 | 3.1 | 3.2 | 4.0 | 4.5 | 5.6 | 6.2 | 8.2 | 9.2 | 11.2 | 12.8 |
| Sample 4 | 3.2 | 3.1 | 3.8 | 4.3 | 5.8 | 6.4 | 8.5 | 9.9 | 11.6 | 13.9 |
| Sample 5 | 3.1 | 3.2 | 4.1 | 4.4 | 5.3 | 6.6 | 8.1 | 9.3 | 11.2 | 13.3 |
| Mean value | 3.1 | 3.1 | 4.0 | 4.3 | 5.5 | 6.4 | 8.4 | 9.4 | 11.4 | 13.5 |

The following conclusions may be analyzed and summarized from the above table. As the proportion of PLLGA increases from 0% to 100%, the higher the proportion, the greater the anti-slip pulling force, which is significant for firmly clamping the clamped object.

Clamping range and brittle fracture performance test is performed. As shown in FIG. 14, the ligating clip is used to clamp cylindrical metal rods with different diameters, and it is observed whether it may be closed smoothly. The larger the diameter of the metal rod that may be smoothly clamped, the better the performance. If it cannot be smoothly clamped or breaks brittlely, it indicates that it may not be used normally under this diameter. If the material formulation of the ligating clip is different, the clamping range of the ligating clip will be different.

Table 11 shows the closing situation of clamping a metal rod with a diameter of 2.0 mm. In which, "√" indicates smooth clamping, and "x" indicates that it cannot be clamped.

TABLE 11

Closing situation of clamping a metal rod with a diameter of Φ2.0 mm

| | PLLGA ratio (wt %) | | | | | | | | | |
|---|---|---|---|---|---|---|---|---|---|---|
| | 0 | 10 | 15 | 20 | 30 | 40 | 50 | 60 | 80 | 100 |
| Sample 1 | ✓ | ✓ | ✓ | ✓ | ✓ | ✓ | ✓ | ✓ | x | x break |
| Sample 2 | ✓ | ✓ | ✓ | ✓ | ✓ | ✓ | ✓ | x | ✓ | x break |
| Sample 3 | ✓ | ✓ | ✓ | ✓ | ✓ | ✓ | ✓ | ✓ | x break | x break |
| Sample 4 | ✓ | ✓ | ✓ | ✓ | ✓ | ✓ | ✓ | ✓ | x | x break |

The size of the pipeline tissue actually clamped by the ligating clip model designed in this experiment during the operation, after the soft tissue is compacted, has a maximum diameter of approximately 1 millimeter. Therefore, the diameter of the 2.0-millimeter metal rod used in this experiment is relatively large, and it is only used to test the trend of the clamping range of the ligating clip changing with the material formulation.

It may be seen from the above test that the higher the proportion of PLLGA, the weaker its elasticity, the greater the plastic deformation after semi-closure, and the higher the possibility of brittle fracture during clamping, which affects the use effect. However, the higher the proportion of PLLGA, the higher the hardness, the greater the clamping force, and the stronger the anti-slip ability, which is beneficial to the use effect.

Based on a comprehensive analysis of the test results of the above three important parameters, and also considering the test conclusions of other performance parameters, it is believed through analysis that when the proportion of the PLLGA material is in the range of 0 wt % to 80 wt %, the performance exhibited by the ligating clip has practical value. However, when the proportion of the PLLGA material is in the range of 0 wt % to 40 wt % (at this time, the corresponding proportion of the PPDO material is 60 wt % to 100 wt %), the performance of the ligating clip is the best and it has the greatest practical value for surgical use.

The ligating clip provided in the present disclosure may effectively address the defects of poor toughness in similar materials and poor hardness in existing absorbable ligating clip materials. It may pierce through the fascia during use and improve its mechanical property.

Embodiment 3

In this embodiment, a ligating clip with antibacterial efficacy is provided, which includes a ligating clip body having the same structure as the ligating clip in embodiment 2. During the preparation process, the antibacterial agent is uniformly dispersed in the raw material first. After processing or injection molding, the antibacterial agent is uniformly distributed throughout the ligating clip, and may be released slowly during the degradation process of the ligating clip body. The weight of the antibacterial agent accounts for 0.1 wt % to 10 wt % of the total weight of the ligating clip body.

During the surgical procedure, bacteria in the surrounding air may enter the surgical site and adhere to the medical device. Specifically, bacteria may spread through the implanted medical device as a pathway to enter the surrounding tissues. The bacteria colonized on the medical device may cause infections and traumas to the patients. Therefore, in order to avoid similar complications during the ligation surgery, an antibacterial agent may be added to the raw material in advance during the preparation of the ligating clip, such that the antibacterial agent is uniformly distributed in the ligating clip body. The antibacterial agent may be a halogenated hydroxy ether, an acyloxy diphenyl ether, a vanillin, an ethyl vanillin compound, an acyl aniline, an imidazole, a thiazole, an isothiazolone derivative, a quaternary ammonium salt, a biguanide, a phenol, or their combinations. The antibacterial agent may also be a nanoparticle containing any metal ions such as silver, cerium, zinc, etc., The antibacterial agent may also be one or more of a tetracycline hydrochloride, a neomycin sulfate, a chloramphenicol, a streptomycin sulfate, a penicillin potassium, an oxytetracycline hydrochloride, a gentamicin sulfate, a cephalothin sodium, a furanone, a rifamycin, a benzalkonium chloride, an oxacillin sodium, a dihydrostreptomycin sulfate, a carbenicillin disodium, and a nitrofurantoin sodium. Preferably, the antibacterial agent is 2,4,4'-trichloro-2'-hydroxydiphenyl ether, commonly known as triclosan. Triclosan is a broad-spectrum antibacterial agent that has been used in a variety of products and may effectively combat common microorganisms. These microorganisms include, but are not limited to, *Staphylococcus, Staphylococcus epidermidis, Staphylococcus aureus*, methicillin-resistant *Staphylococcus aureus*, methicillin-resistant *Staphylococcus aureus*, and combinations thereof.

The antibacterial agent is uniformly dispersed into the raw materials or the ligating clip body by methods such as solvent treatment, melting, extrusion granulation, physical mixing or injection molding. The content of the antibacterial agent in the antibacterial ligating clip is approximately 0.1 wt % to 10 wt %. As the ligating clip degrades, the antibacterial agent is gradually released slowly.

In this embodiment, triclosan is used as the antibacterial agent, and the ligating clip of the first structural form in embodiment 2 (in which the content of PLLGA is 40 wt %) is used as the ligating clip body. Antibacterial ligating clips with antibacterial agent contents of 0.1 wt %, 5 wt % and 10 wt % are respectively formed by the melt injection molding method. Then, typical Gram-negative bacteria (*Escherichia coli*) and Gram-positive bacteria (*Staphylococcus aureus*) are selected to study the antibacterial ability of the antibacterial ligating clip.

The specific process of the antibacterial test includes the follows. Firstly, 0.1 mL of the degradation solution around the antibacterial ligating clip is placed in a 24-well plate and sterilized in an ultraviolet environment for 24 hours. Then, 1 mL of bacterial suspension containing *Escherichia coli* and *Staphylococcus aureus* with a concentration of $10^6$ CFU/mL is added to each sample. After incubation at 37° C. for 6 hours, the liquid in the 24-well plate is stirred uniformly to form a mixed solution. 450 μL of nutrient broth medium is added to a 48-well culture plate, and then 50 μL of the above mixed solution is taken out and added to the 48-well culture plate respectively. Five parallel samples are set for each group of experiments. After culturing for 24 hours under the same conditions, 100 μL of the liquid is aspirated and added to a 96-well plate, and the absorbance of the liquid at a wavelength of 630 nm is measured with a microplate reader. The bacteria without the addition of the degradation solution are used as the control group. The nutrient broth medium is used as the blank.

The bacterial killing rate (%) is calculated using the following formula:

$$\text{Bacterial kill (\%)} = 1 - \frac{A_{sample} - A_{blank}}{A_{control} - A_{blank}} \times 100\%$$

$A_{sample}$, $A_{control}$, and $A_{blank}$ are the absorbance of the material group, the absorbance of the control group, and the absorbance of the nutrient broth, respectively.

The antibacterial test shows that the antibacterial ligating clips in this embodiment have a bactericidal rate of approximately 25%, 59%, and 87.2% against *Staphylococcus aureus*, and a bactericidal rate of around 13%, 42%, and 73% against *Escherichia coli*, demonstrating antibacterial abilities at different levels. The specific antibacterial test data are shown in Table 12 below.

TABLE 12

Statistical table of the bactericidal rate of antibacterial ligating clips

| Antimicrobial agent content | Strain: Bactericidal rate % (*Staphylococcus aureus*) Number 1 | 2 | 3 | 4 | 5 | Bactericidal rate % (*Escherichia coli*) Number 1 | 2 | 3 | 4 | 5 |
|---|---|---|---|---|---|---|---|---|---|---|
| 0.1 wt % | 28 | 21 | 22 | 29 | 25 | 16 | 11 | 15 | 11 | 12 |
| 5.0 wt % | 60 | 59 | 62 | 55 | 59 | 44 | 41 | 40 | 40 | 45 |
| 10 wt % | 85 | 82 | 89 | 90 | 91 | 71 | 72 | 70 | 75 | 77 |
| Control group (without antimicrobial agent) | 0 | 0 | 0 | 0 | 0 | 0 | 0 | 0 | 0 | 0 |

It may be known from the above experimental tests that the ligating clip disclosed in the present disclosure may effectively kill bacteria to a certain extent after the antibacterial agent is added.

Embodiment 4

In this embodiment, the ligating clip with antibacterial efficacy is provided, which includes a ligating clip body having the same structure as the ligating clip in embodiment 2, and an antibacterial layer attached to the surface of the ligating clip body. The weight of the antibacterial layer accounts for 0.1 wt % to 3 wt % of the total weight of the antibacterial ligating clip. Compared with embodiment 3, the antibacterial efficacy of the antibacterial ligating clip in this embodiment is mainly achieved through the antibacterial layer attached to the surface of the ligating clip body.

In this embodiment, the antibacterial agent in the composition of the antibacterial layer may be one or a combination of a halogenated hydroxy ether, an acyloxy diphenyl ether, a vanillin, an ethyl vanillin compound, an acyl aniline, an imidazole, a thiazole, an isothiazolone derivative, a quaternary ammonium salt, a biguanide, and a phenol. The antibacterial agent in the composition of the antibacterial layer may also be a nanoparticle containing any metal ions such as silver, cerium, zinc, etc. The antibacterial agent in the composition of the antibacterial layer may also be one or more of a tetracycline hydrochloride, a neomycin sulfate, a chloramphenicol, a streptomycin sulfate, a penicillin potassium, an oxytetracycline hydrochloride, a gentamicin sulfate, a cephalothin sodium, a furanone, a rifamycin, a benzalkonium chloride, an oxacillin sodium, a dihydrostreptomycin sulfate, a carbenicillin disodium, and a nitrofurantoin sodium. Preferably, the antibacterial agent is 2,4,4'-trichloro-2'-hydroxydiphenyl ether, commonly known as triclosan. Triclosan is a broad-spectrum antibacterial agent that has been used in a variety of products and may effectively combat common microorganisms. These microorganisms include, but are not limited to, *Staphylococcus, Staphylococcus epidermidis, Staphylococcus aureus*, methicillin-resistant *Staphylococcus aureus*, methicillin-resistant *Staphylococcus aureus*, and combinations thereof. In addition to the antibacterial agent, the composition of the antibacterial layer may further include an adhesive (such as a lactide and glycolide polymer) and a lubricant (such as calcium stearate).

In this embodiment, the antibacterial layer is formed by an impregnation method. The process involves dissolving the antimicrobial agent in a suitable solvent to create an impregnation solution, immersing the ligating clip body into the solution, and then drying the impregnated ligating clip body to remove the solvent. As a result, the residual antimicrobial agent forms a uniform coating on the surface of the clip body. The concentration of the antibacterial agent in the impregnation solution is approximately 2 wt % to 15 wt %, and the content of the antibacterial agent in the finally formed antibacterial ligating clip is approximately 0.1 wt % to 3 wt %.

In this embodiment, triclosan is used as the antibacterial agent, and the ligating clip of the first structural form in embodiment 2 (in which the content of PLLGA is 40 wt %) is used as the ligating clip body. Antibacterial ligating clips with antibacterial agent contents of 0.1 wt %, 2 wt %, and 3 wt % are respectively formed by the impregnation method. Then, typical Gram-negative bacteria (*Escherichia coli*) and Gram-positive bacteria (*Staphylococcus aureus*) are selected to study the antibacterial ability of the antibacterial layer.

The specific process of the antibacterial test includes the following. Firstly, the antibacterial ligating clip is placed in a 24-well plate and sterilized in an ultraviolet environment for 24 hours. Then, 1 mL of bacterial suspension containing *Escherichia coli* and *Staphylococcus aureus* with a concentration of $10^6$ CFU/mL is added to each sample. After incubation at 37° C. for 6 hours, the liquid in the 24-well plate is stirred uniformly to form a mixed solution. 450 μL of nutrient broth medium is added to a 48-well culture plate, and then 50 μL of the above mixed solution is taken out and added to the 48-well culture plate respectively. Five parallel samples are set for each group of experiments. After culturing for 24 hours under the same conditions, 100 μL of the liquid is aspirated and added to a 96-well plate, and the absorbance of the liquid at a wavelength of 630 nm is measured with a microplate reader. The bacteria that have not been treated with the antibacterial ligating clip are used as the control group. The nutrient broth medium is used as the blank.

The bacterial killing rate (%) is calculated using the following formula:

$$\text{Bacterial kill }(\%) = 1 - \frac{A_{sample} - A_{blank}}{A_{control} - A_{blank}} \times 100\%$$

$A_{sample}$, $A_{control}$, and $A_{blank}$ are the absorbance of the material group, the absorbance of the control group, and the absorbance of the nutrient broth, respectively.

The antibacterial test shows that the antibacterial ligating clips in this embodiment have a bactericidal rate of approximately 37%, 74%, and 97% against *Staphylococcus aureus*, and a bactericidal rate of around 20%, 51%, and 83% against *Escherichia coli*, demonstrating antibacterial abilities at different levels. The specific antibacterial test data are shown in Table 13 below.

TABLE 13

Statistical table of the bactericidal rate of antibacterial ligating clips

| Antimicrobial agent content | Strain: Bactericidal rate % (*Staphylococcus aureus*) Number 1 | 2 | 3 | 4 | 5 | Bactericidal rate % (*Escherichia coli*) Number 1 | 2 | 3 | 4 | 5 |
|---|---|---|---|---|---|---|---|---|---|---|
| 0.1 wt % | 35 | 39 | 41 | 36 | 34 | 21 | 19 | 17 | 20 | 23 |
| 2.0 wt % | 79 | 76 | 69 | 72 | 74 | 55 | 50 | 49 | 51 | 50 |
| 3.0 wt % | 99 | 97 | 95 | 99 | 98 | 81 | 82 | 80 | 85 | 87 |
| Control group (without antimicrobial agent) | 0 | 0 | 0 | 0 | 0 | 0 | 0 | 0 | 0 | 0 |

It may be known from the above experimental tests that the ligating clip disclosed in present disclosure may effectively kill bacteria to a certain extent after the antibacterial agent is added.

What is claimed is:

1. A ligating clip, made from an absorbable biomedical polymer material, the absorbable biomedical polymer material comprising a first polymer and a second polymer, and wherein:

with a sum of weight percentages being 100%, a weight ratio of the first polymer is 2.5 wt % to 60 wt %, and a weight ratio of the second polymer is 40 wt % to 97.5 wt %;

the first polymer is composed of poly-L-lactide with a weight ratio of 50 wt % to 100 wt % and polyglycolide with a weight ratio of 0 wt % to 50 wt %;

the second polymer is poly-p-dioxanone; and the absorbable biomedical polymer material has a tensile strength of 27 to 95.7 MPa, a flexural strength of 23 to 164 MPa, a compressive strength of 95 to 557 MPa, and a Vickers hardness of 2.5 to 19.5 HV.

2. The ligating clip according to claim 1, wherein the weight ratio of the first polymer is 2.5 wt % to 50 wt %, and the weight ratio of the second polymer is 50 wt % to 97.5 wt %.

3. The ligating clip according to claim 2, wherein the weight ratio of the first polymer is 2.5 wt % to 40 wt %, and the weight ratio of the second polymer is 60 wt % to 97.5 wt %.

4. The ligating clip according to claim 1, wherein the first polymer is composed of the poly-L-lactide with the weight ratio of 70 wt % to 100 wt % and the polyglycolide with the weight ratio of 0 wt % to 30 wt %.

5. A ligating clip, made from a same material as the ligating clip according to claim 1, wherein the ligating clip comprises:

a ligating clip body;

the ligating clip body comprising a clip and a locking device for keeping the clip closed;

the clip having a first clip arm and a second clip arm connected in a V-shape, the first clip arm and the second clip arm being in a curved arc structure with a same direction, or the first clip arm and the second clip arm being in a straight structure;

the locking device comprising a hook portion arranged at a distal end of the first clip arm and a fitting portion arranged at a distal end of the second clip arm and adapted to the hook portion, the hook portion being provided with an acute-angle cutting structure or a linear sharp-edge cutting structure; and two limit blocks, the two limit blocks being oppositely arranged at the distal end of the second clip arm; and the hook portion being engaged with the two limit blocks and limited between the two limit blocks.

6. The ligating clip according to claim 5, wherein:

in accordance with a determination that the first clip arm and the second clip arm are in the curved arc structure with the same direction;

a connection between the first clip arm and the second clip arm is provided with a hollow groove; and an inner side of the hook portion is provided with a reinforcing rib.

7. The ligating clip according to claim 5, wherein:

the clip is provided with a clamping device;

the clamping device comprises a first clamping column arranged on left and right sides of the distal end of the first clip arm along a width direction of the clip; or the clamping device comprises a first clamping column arranged on left and right sides of the distal end of the first clip arm along a width direction of the clip; and a second clamping column arranged on left and right sides of the distal end of the second clip arm along the width direction of the clip.

8. The ligating clip according to claim 5, wherein:

the clip is provided with a positioning device;

the positioning device comprises a first positioning groove provided on an inner side of the distal end of the first clip arm and a first positioning protrusion provided on an inner side of the second clip arm and adapted to the first positioning groove; and/or the positioning device comprises a second positioning protrusion provided on an outer side of the distal end of the second clip arm and a second positioning groove provided on an outer side of the first clip arm and adapted to the second positioning protrusion.

9. The ligating clip according to claim 5, wherein:

the locking device is provided with a penetrating device configured to cut a tissue when the clip begins to close;

the penetrating device comprises a pointed cutting head provided at an outer end of the hook portion;

when the clip begins to close, the pointed cutting head cooperates with an inclined surface on the fitting portion to cut the tissue.

10. The ligating clip according to claim 5, wherein:

a surface of the ligating clip body is attached with an antibacterial layer, the antibacterial layer comprises an antibacterial agent, and a weight of the antibacterial agent is 0.1 wt % to 3 wt % of a total weight of the ligating clip body; or the ligating clip body is uniformly dispersed with an antibacterial agent, a weight of the antibacterial agent is 0.1 wt % to 10 wt % of a total weight of the ligating clip body.

11. The ligating clip according to claim 10, wherein:

the antibacterial agent is one or more of a halogenated hydroxy ether, an acyloxy diphenyl ether, a vanillin, an ethyl vanillin compound, an acyl aniline, an imidazole, a thiazole, an isothiazolone derivative, a quaternary ammonium salt, a biguanide, and a phenol.

12. The ligating clip according to claim 10, wherein the antibacterial agent is a nanoparticle containing any one or a combination of metal ions selected from group consisting of silver, cerium, and zinc.

13. The ligating clip according to claim 10, wherein the antibacterial agent is one or more of a tetracycline hydrochloride, a neomycin sulfate, a chloramphenicol, a streptomycin sulfate, a penicillin potassium, an oxytetracycline hydrochloride, a gentamicin sulfate, a cephalothin sodium, a furanone, a rifamycin, a benzalkonium chloride, an oxacillin sodium, a dihydrostreptomycin sulfate, a carbenicillin disodium, and a nitrofurantoin sodium.

14. The ligating clip according to claim 10, wherein the antibacterial agent is 2,4,4'-trichloro-2'-hydroxydiphenyl ether.

15. A ligating clip, made from a same material as the ligating clip according to claim 1, wherein the ligating clip comprises:

a ligating clip body, the ligating clip body comprising an inner clip and an outer clip with a U shape;

content of a first polymer in the outer clip is greater than content of the first polymer in the inner clip.

16. The ligating clip according to claim 15, wherein:

an outer wall of the inner clip has a groove along a length direction of the inner clip, and an inner wall of a U-shaped area of the outer clip has a rib matching with the groove;

when the rib is inserted into the groove and slides along the groove, the inner clip is forcibly deformed within the outer clip to complete clamping.

17. The ligating clip according to claim 15, wherein:

a surface of the ligating clip body is attached with an antibacterial layer, the antibacterial layer comprises an antibacterial agent, and a weight of the antibacterial agent accounts for 0.1 wt % to 3 wt % of a total weight of the ligating clip body; or the ligating clip body is uniformly dispersed with an antibacterial agent, and a weight of the antibacterial agent accounts for 0.1 wt % to 10 wt % of a total weight of the ligating clip body.

18. The ligating clip according to claim 17, wherein:

the antibacterial agent is one or more of a halogenated hydroxy ether, an acyloxy diphenyl ether, a vanillin, an ethyl vanillin compound, an acyl aniline, an imidazole, a thiazole, an isothiazolone derivative, a quaternary ammonium salt, a biguanide, and a phenol;

or the antibacterial agent is 2,4,4'-trichloro-2'-hydroxydiphenyl ether.

19. The ligating clip according to claim 17, wherein the antibacterial agent is a nanoparticle containing any one or a combination of metal ions selected from the group consisting of silver, cerium, and zinc.

20. The ligating clip according to claim 17, wherein the antibacterial agent is one or more of a tetracycline hydrochloride, a neomycin sulfate, a chloramphenicol, a streptomycin sulfate, a penicillin potassium, an oxytetracycline hydrochloride, a gentamicin sulfate, a cephalothin sodium, a furanone, a rifamycin, a benzalkonium chloride, an oxacillin sodium, a dihydrostreptomycin sulfate, a carbenicillin disodium, and a nitrofurantoin sodium.

* * * * *